United States Patent
Ishige et al.

(10) Patent No.: US 8,702,933 B2
(45) Date of Patent: Apr. 22, 2014

(54) POTENTIOMETRIC SENSOR AND ANALYTICAL ELEMENT

(75) Inventors: Yu Ishige, Tokyo (JP); Masao Kamahori, Kokubunji (JP)

(73) Assignee: Hitachi, Ltd., Tokyo (JP)

(*) Notice: Subject to any disclaimer, the term of this patent is extended or adjusted under 35 U.S.C. 154(b) by 0 days.

(21) Appl. No.: 13/523,292

(22) Filed: Jun. 14, 2012

(65) Prior Publication Data

US 2012/0261259 A1 Oct. 18, 2012

Related U.S. Application Data

(62) Division of application No. 11/942,862, filed on Nov. 20, 2007, now Pat. No. 8,202,409.

(30) Foreign Application Priority Data

Nov. 21, 2006 (JP) ................................. 2006-313876

(51) Int. Cl.
*G01N 27/26* (2006.01)

(52) U.S. Cl.
USPC ... 204/403.14; 204/435; 204/400; 435/287.1; 422/68.1; 422/82.01

(58) Field of Classification Search
USPC .................. 204/403.01–403.15, 435, 400; 205/777.5; 257/253, 288, 350, 390; 422/82.01, 68.1; 435/287.1
See application file for complete search history.

(56) References Cited

U.S. PATENT DOCUMENTS

| | | | |
|---|---|---|---|
| 4,437,969 A | 3/1984 | Covington et al. | |
| 4,877,582 A | 10/1989 | Oda et al. | |
| 4,968,400 A | 11/1990 | Shimomura et al. | |
| 6,455,873 B1* | 9/2002 | Lonergan | 257/40 |
| 7,348,854 B1* | 3/2008 | Mordkovich | 330/298 |
| 2003/0073071 A1 | 4/2003 | Fritz et al. | |
| 2004/0219523 A1 | 11/2004 | Stanton et al. | |
| 2005/0156207 A1 | 7/2005 | Yazawa et al. | |
| 2005/0164286 A1 | 7/2005 | O'uchi et al. | |

(Continued)

FOREIGN PATENT DOCUMENTS

| | | |
|---|---|---|
| JP | 03-137552 | 6/1991 |
| JP | 09-500727 | 1/1997 |

(Continued)

OTHER PUBLICATIONS

Chidsey et al. (J. Am. Chem. Soc. 1990, vol. 112, pp. 4301-4306).*

(Continued)

*Primary Examiner* — Jennifer Dieterle
(74) *Attorney, Agent, or Firm* — Antonelli, Terry, Stout & Kraus, LLP.

(57) ABSTRACT

A potentiometric sensor with suppressed leak current on the surface of an electrode and improved for a dynamic range and a response speed, in which a redox compound is immobilized through insulative molecules on the surface of a gold electrode, and a current between a source and drain of an insulated gate field-effect transistor along with reaction between an oxidized substance or a reduced substance produced by the reaction of a measured substance in a sample solution injector for supplying the sample solution containing the measured substance and an enzyme and a redox compound on the surface of the gold electrode, is monitored on real time to measure the change of the surface potential.

7 Claims, 15 Drawing Sheets

(56) References Cited

U.S. PATENT DOCUMENTS

2006/0016699 A1* 1/2006 Kamahori et al. ......... 205/777.5
2006/0141474 A1 6/2006 Miyahara et al.
2006/0223170 A1 10/2006 Kamahori et al.

FOREIGN PATENT DOCUMENTS

WO  WO 95/03543     2/1995
WO  WO 2005-022142  3/2005
WO  WO2005-066618 * 7/2005

OTHER PUBLICATIONS

Nguyen et al. (Applied Biochemistry and Biotechnology, vol. 43, 1993, 117-132).*
BAS Operations Manual 1984.*
Willner, et al., "Development of Novel Biosensor Enzyme Electrodes: Glucose Oxidase Multilayer Arrays Immobilized onto Self-Assembled Monolayers on Electrodes", Advanced Materials 5(1993) 912-915.
Erickson, et al., "Evaluation of a Novel Point-of-Care System, the i-Stat Portable Clinical Analyzer", Clinical Chemistry 39/2 (1993) 283-287.
Chidsey et al. (J. Am. Chem. Soc. 1990, vol. 112, pp. 4301-4306.
Shimomura Derwent English Abstract 1991.
Souteyrand et al. (J. Pys. Chem B 1997, 101, 2980-2985).
Ahn et al. (IEEE Sensors Journal, vol. 2, No. 1, Feb. 2002, pp. 26-33.

* cited by examiner

POTENTIOMETRIC SENSOR AND ANALYTICAL ELEMENT

CLAIM OF PRIORITY

The present application claims priority from Japanese application JP 2006-313876 filed on Nov. 21, 2006, the content of which is hereby incorporated by reference into this application.

This application is a Divisional application of application Ser. No. 11/942,862, filed Nov. 20, 2007, now U.S. Pat. No. 8,202,409, the contents of which are incorporated herein by reference in their entirety.

FIELD OF THE INVENTION

The present invention concerns a sensor and an analytical element capable of measuring a biological substance at a high sensitivity by subjecting a biological substance selectively to redox reaction using an enzyme or the like and measuring the surface potential formed therein.

BACKGROUND OF THE INVENTION

Blood test in health check is effective for recognizing the state of heath and early detection of a disease. In the blood test upon health check, since a large number of samples are analyzed over multiple targets, large-scaled clinical analyzers are used. Since the clinical analyzers are expensive and have to be operated by expert engineers, they are introduced in large-scaled hospitals or blood testing centers, but are not placed in general clinics. Accordingly, when blood test is performed in a general clinic, it usually takes several days for obtaining the result. This time lag causes no problem in the case of health checks since most of them are performed at a frequency of once per year or one half year. In an urgent case, however, it is necessary to conduct blood test on the spot. For example, during surgery, it is necessary to monitor blood electrolytes such as sodium, potassium, or chlorine, an oxygen partial pressure, a carbon dioxide gas partial pressure, glucose, blood urea nitrogen, hematocrit. Further, in dialysis for renal insufficiency, creatinine is measured. In addition to such urgent testing, it is also a demand for point of care testing (POCT) in order to check the health state in general clinics. The apparatus coping with such demand is a POCT apparatus, which has an advantage capable of testing on-site optionally although the number of test targets and throughputs are not so favorable as those of the clinical analyzer. The test targets include electrolyte, glucose, cholesterol, lactic acid, blood urea nitrogen, and creatinine. For general chemical measurement for glucose, cholesterol, lactic acid, blood urea nitrogen, and creatinine other than the electrolyte, an enzyme electrode method is used.

The enzyme electrode method is a method of measuring the concentration of the substance, which is converted into another substance capable of being measured by an electrode using an enzymatic reaction, indirectly by the electrode as a current or potential change. For example, in a glucose sensor for measuring a blood glucose level, glucose as a substance to be measured is oxidized by a glucose oxidase and gluconolactone is produced. By the oxidation reaction, oxygen is consumed to produce hydrogen peroxide. Since both oxygen and hydrogen peroxide are redox active compounds, the concentration of the glucose as the substance to be measured can be measured by using an oxygen electrode or a hydrogen peroxide electrode as the electrode current. However, in a case where the glucose is at a high concentration, the rate of oxidation reaction is sometimes limited by the concentration of dissolved (partial pressure) oxygen in the blood. As a countermeasure, other redox compound is sometimes used instead of oxygen. Other chemical substances can also be measured on a similar principle. Such a type of sensor is generally referred to as an amperometric enzyme sensor.

In the amperometric enzyme sensor, a working electrode, formed of gold, platinum or the like, a counter electrode and a reference electrode for keeping the potential of the working electrode constant are arranged in a solution, and an enzyme and a redox compound are in the solution. The working electrode, the counter electrode, and the reference electrode are connected to a current measuring device such as a potentiostat, such that a current value which changes upon application of a voltage between the working electrode and the counter electrode can be measured. When a sample (for example, blood) containing a substance to be measured is added to the solution, the substance is oxidized by the enzyme and, at the same time, the redox compound in the oxidized state is reduced. When a constant voltage capable of oxidizing the redox compound is applied to the working electrode, the redox compound in the reduced state is oxidized on the working electrode and a current flows in accordance with the concentration of the redox compound in the reduced state. In this way, the oxidation reaction of the substance to be measured by the enzyme can be measured as a current, and the concentration of the substance to be measured can be measured indirectly. In this case, it is necessary for an enzyme at a sufficient concentration, a redox compound at a sufficient concentration, and a working electrode of a sufficient size such that a current value in accordance with the concentration of the substance to be measured can be obtained, that is, the concentration of the substance to be measured is a rate determining factor in the reaction system.

In the amperometric enzyme sensor, an enzyme is immobilized on a membrane mainly with an aim of re-utilizing the enzyme. However, in a case where the enzyme is immobilized, since the reaction efficiency of the enzyme and the substance to be measured and the enzyme and the redox compound is lowered, the redox compound is immobilized together with the enzyme on the membrane at the surface of the working electrode (Adv. Mater. 5(1993) 912-915). It is considered that lowering of the transfer efficiency of charges from the enzyme to the redox compound can be suppressed by immobilizing the enzyme together with the redox compound on the membrane at the surface of the electrode. Further, by immobilizing the enzyme and the redox compound at a multilayer, the sensitivity is improved more and lowering of the reaction efficiency between the enzyme and the object to be measured can be suppressed compared with a case of a monolayer.

In the glucose sensor for measuring the blood glucose level, since a necessary measuring sensitivity is not so high, measuring is possible with a blood amount of several droplets. However, in a POCT apparatus for general targets, more amount of blood is necessary for maintaining the measuring sensitivity. For example, i-Stat developed as a POCT apparatus (Clin. Chem. 39/2 (1993) 283-287) required a blood amount of about 65 µl. While the blood amount can be decreased by making the electrode area smaller, since a signal (that is, current value) decreases as the electrode area is made smaller in the amperometric enzyme sensor, it was difficult to simply decrease the electrode area.

A potentiometric enzyme sensor is known as an enzyme sensor using an electric measuring method in which signals do not depend on the electrode area. The potentiometric enzyme sensor consists of a working electrode formed of gold, platinum, etc. and a reference electrode in which an enzyme and a redox compound are present in the measuring solution (JP-T No. 9-500727). Further, the working electrode and the reference electrode are connected to a device for measuring voltage. When a substance to be measured is added to the measuring solution, the substance to be measured is oxidized by an enzymatic reaction and, at the same time, a redox compound in an oxidized state is reduced. The surface potential on the working electrode generated in this case is in accordance with the following Nernst's equation.

$$E = E^0 + \frac{RT}{nF}\ln(C_{ox}/C_{red})$$ [Formula 1]

where
E: surface potential of working electrode,
$E^0$: reference potential of redox compound
R: gas constant
T: absolute temperature
n: difference of charges between oxidized state and reduced state of redox compound
F: Faraday constant
$C_{ox}$: concentration of oxidized state of redox compound
$C_{red}$: concentration of reduced state of redox compound As can be seen from the equation described above, the change of the surface potential does not depend on the electrode area. Further, unlike the amperometric enzyme sensor, since a voltage is not applied to the working electrode, chemical reaction interfering the measurement less occurs. Further, since the voltage changes as the logarithm of the concentration as shown in the equation described above, a substance can be measured also in a low concentration region at an S/N ratio identical with that in a high concentration region and it is considered that a wider dynamic range can be obtained compared with the amperometric enzyme sensor.

However, in the existent potentiometric enzyme sensor, consideration is not taken on the insulative property between the working electrode and the measuring solution, and it involved a problem that actual measurement undergoes the effect of a leak current on the surface of the electrode and the sensitivity is lowered, particularly, in the low concentration region, the dynamic range narrowed and, further, the response speed is lowered.

SUMMARY OF THE INVENTION

The present invention intends to provide a potentiometric sensor of suppressing a leak current at the surface of an electrode which causes a problem in actual measurement and improving a dynamic range and a response speed.

This is attained according to the present invention by immobilizing a redox compound through insulative molecules on the surface of the working electrode not allowing the current to flow, for example, a carbon chain and measuring the change of a surface potential along with the reaction of an oxidation substance or a reduction substance produced by the reaction between a substance to be measured and an enzyme and a redox compound on the surface of the working electrode. Further, as a potentiometric device, an insulated gate field-effect transistor formed on a substrate identical with that for the working electrode is used.

According to the invention, by immobilizing the redox compound through the insulative molecules on the surface of the working electrode, a working electrode having a property responsible to an oxidized substance or a reduced substance in a solution and having a high insulative property to the solution can be obtained. Improvement in the insulative property can suppress the leak current on the surface of the electrode, particularly, improve the sensitivity in the low concentration region and can extend a dynamic range, as well as the response speed can be increased. Further, hydrogen peroxide or a thiol compound that could not be measured repetitively so far by the potential difference can be measured repetitively by the potential difference. Then, since the apparent concentration of the redox compound does not depend on the amount of the solution, measurement is possible not depending on the amount of the blood. By using an insulated gate filed-effect transistor formed on a substrate identical with that for the working electrode as a potentiometric device, the leak can be decreased, dynamic range can be extended and the response speed can be improved. Further, by immobilizing the redox compound on the working electrode with insulative molecules of an identical length, working electrode can obtain insulative property and change of state of the immobilized redox compound can give an effect on the surface potential of the working electrode uniformly.

DETAILED DESCRIPTION OF THE PREFERRED EMBODIMENTS

The present invention is to be described by way of preferred embodiments with reference to the drawings.

Figure 1:
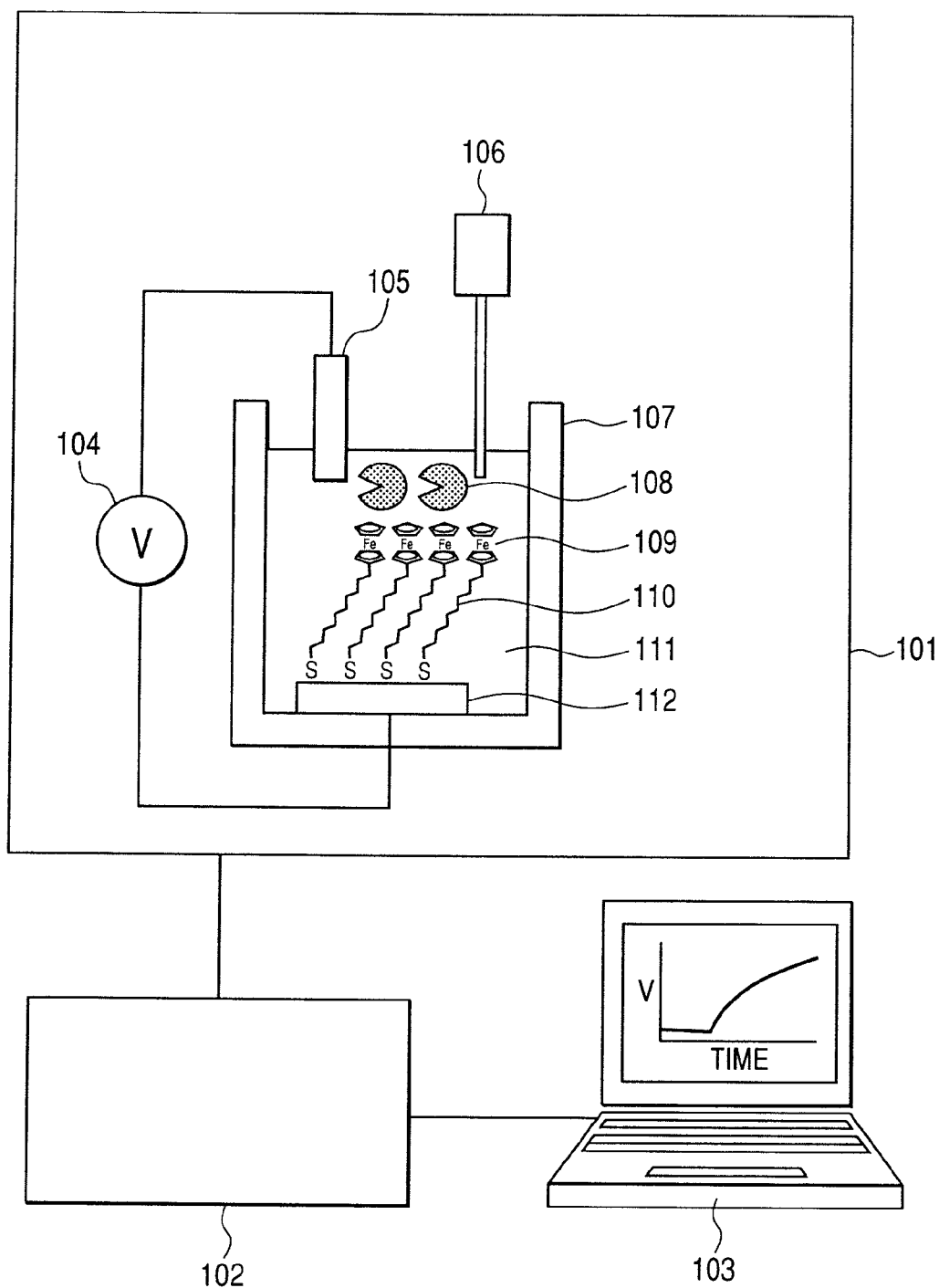
FIG. 1 is a block diagram showing an example of a potentiometric enzyme sensor according to the invention.

FIG. 1 is a block diagram showing an example of a potentiometric enzyme sensor according to the invention. The measuring system of this embodiment includes a measuring station 101, a signal processing circuit 102, and a data processing apparatus 103. The measuring station 101 has a potentiometric device 104, a reference electrode 105, a sample solution injector 106 for supplying a sample solution containing a substance to be measured, and a measuring cell 107. In the measuring solution 111 in the measuring cell 107, there are placed an enzyme 108, a gold electrode 112 on which a redox compound 109 is immobilized through insulative molecules 110 and the reference electrode 105. While an oxidase conducting oxidation and reduction is used as an enzyme, any enzyme that produces an oxidized substance or reduced substance by enzymatic reaction can be used with no problem. For example, acetylcholinesterase that hydrolyzes acetylthiocholine to produces a thiol compound, which is a reduced substance, can also be used.

Measuring procedures are as described below. The sample solution is injected by using the sample solution injector 106 into the measuring solution 111 in the measuring cell 107. A substance to be measured in the sample solution is oxidized by the enzymatic reaction and, along with the reaction, dissolved oxygen in the sample solution is reduced into hydrogen peroxide. The produced hydrogen peroxide oxidizes the redox compound 109. As a result, the potential on the gold electrode 112 changes. The potential difference between the reference electrode 105 and the gold electrode 112 that changes before and after the injection of the sample solution by the sample solution injector 106 is measured at a real time by the potentiometric device 104, and recorded by the signal processing circuit 102 and the data processing apparatus 103. The rate of change of the potential on the gold electrode 112 depends on the rate of producing hydrogen peroxide, that is, the reaction rate of oxidation of the substance to be measured, and the reaction rate of the oxidation of the substance to be measured depends on the concentration of the substance to be measured. Accordingly, by measuring the rate of change of the potential difference between the reference electrode 105 and the gold electrode 112, the concentration of the substance to be measured can be obtained.

Like the rate of change of the potential difference between the reference electrode 105 and the gold electrode 112, the quantity of change of the potential difference between the reference electrode 105 and the gold electrode 112 during a certain period depends on the concentration of the measured substance. Accordingly, the concentration of the substance to be measured can be obtained by measuring the quantity of change between the potential difference before the injection of the sample solution or just after the injection of the sample solution and the potential difference at a predetermined time after the injection of the sample solution. Further, in a case where the reproducibility of the potential difference between the reference electrode 105 and the gold electrode 112 before the injection of the sample solution is higher than the accuracy required for measurement, the concentration of the substance to be measured can be obtained by measuring the potential difference at a predetermined time after the injection of the sample solution.

Preferably, the redox compound 109 is previously in a reduced state in a case of measuring the oxidizing substance such as hydrogen peroxide. For providing a reduced state, it is treated with a reducing agent such as potassium ferrocyanide, sodium thiosulfate or dithiothreitol (DTT), or a reducing potential is applied by using a potentiostat. By applying the reducing treatment, the potential before the injection of the sample solution can be stabilized and, further, the sensitivity at a low concentration can be improved to extend the dynamic range. In the same manner, in a case of measuring the reducing substance such as the thiol compound, it is preferably formed into an oxidized state. For providing the oxidizing state, it is treated by an oxidizing agent such as potassium ferricyanide, potassium permanganate or hydrogen peroxide, or an oxidizing potential is applied by using a potentiostat. By previously applying the oxidizing treatment, the potential before the injection of the sample solution can be stabilized and, further, the sensitivity at a low concentration can be improved to extend the dynamic range.

For the insulative molecules 110, an alkane thiol is used preferably. By the use of the alkane thiol, a highly insulative monolayer can be formed easily on the surface of a noble metal such as gold or silver. With a view point of the insulative property, the alkyl chain in the alkanethiol has a carbon chain of 6 or more.

The reference electrode 105 provides a reference potential for stably measuring the potential change based on an equilibrium reaction or chemical reaction occurring at the surface of the gold electrode 112 in the measuring solution 111. A silver chloride electrode or a calomel electrode using saturated potassium chloride as an internal solution is usually used as the reference electrode. A silver chloride electrode without an internal solution may be used as a quasi-reference electrode.

Instead of the gold electrode 112, an electrode comprising other noble metal such as silver or carbon may also be used.

A sample solution is not present in the measuring solution 111 before injection of the sample solution but a sample solution supplied from the sample solution injector 106 may function as such solution. In this case, the enzyme 108 may be previously solidified by freeze drying or the like and dissolved by a sample solution supplied from the sample solution injector 106.

For oxidation and reduction of the measured substance by the enzyme 108, an enzyme for the pretreatment of the measured substance or a substrate needed for redox reaction may sometimes be used.

The enzyme 108 in accordance with the measured substance and the enzyme for the pretreatment are exemplified in Table 1.

TABLE 1

| Target | Enzyme |
|---|---|
| Glucose | Glucose oxidase |
| Cholesterol | Cholesterol oxidase (for pretreatment: cholesterol esterase) |

TABLE 1-continued

| Target | Enzyme |
| --- | --- |
| Lactate | Lactate oxidase |
| Creatine | Sarcosine oxidase (for pretreatment: creatinase) |
| Creatinine | Sarcosine oxidase (for pretreatment: creatininase, creatinase) |
| Pyruvate | Pyruvate oxidase (substrate: phosphoric acid) |
| Hemoglobin $A_{1c}$ | Fructosyl-amino acid oxidase, or fructosyl-peptide oxidase (for pretreatment: protease) |
| Alcohol | Alcohol oxidase |
| Triglyceride | Glycerol oxidase (for pretreatment: Lipase) |

Figure 2:
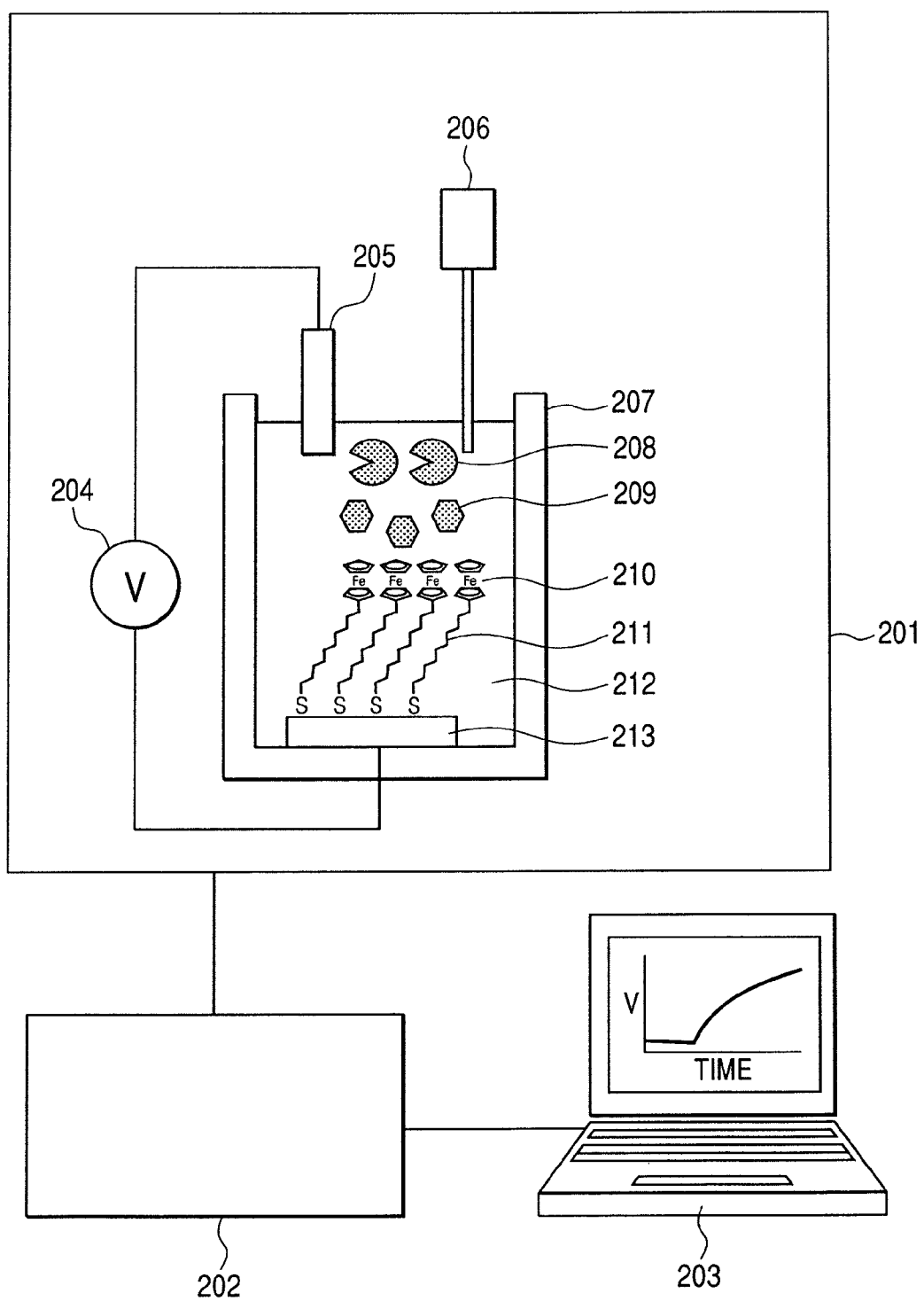
FIG. 2 is a block diagram showing an example of a potentiometric enzyme sensor according to the invention.

FIG. 2 is a block diagram showing an example of a potentiometric enzyme sensor according to the invention. The measuring system of this embodiment includes a measuring station 201, a signal processing circuit 202 and a data processing apparatus 203. The measuring station 201 has a potentiometric device 204, a reference electrode 205, a sample solution injector 206 for supplying a sample solution containing a measured substance, and a measuring cell 107. In the measuring solution 212 in the measuring cell 207, there are placed an enzyme 208, a water soluble redox compound 209 not immobilized on the gold electrode 213, a gold electrode 213 on which a redox compound 210 is immobilized through insulative molecules 211, and the reference electrode 205.

The measuring procedures are as described below. A sample solution is injected by using the sample solution injector 206 into the measuring solution 212 in the measuring cell 207. The measured substance in the sample solution is oxidized by the enzymatic reaction and, along with the reaction, the redox compound 209 in the sample solution is reduced. The produced redox compound 209 in the reduced state oxidizes the redox compound 210. As a result, the potential on the gold electrode 213 changes. The potential difference between the reference electrode 205 and the gold electrode 213 that changes before and after the injection of the sample solution by the sample solution injector 206 is measured at a real time and recorded by the signal processing circuit 202 and the data processing apparatus 203. The rate of change of the potential on the gold electrode 213 depends on the rate of producing the redox compound 209 in the reduced state, that is, the reaction rate of oxidation of the measured substance and the reaction rate of oxidation of the measured substance depends on the concentration of the measured substance. Accordingly, the concentration of the measured substance can be obtained by measuring the rate of change of the potential difference between the reference electrode 205 and the gold electrode 213.

Like the rate of change of the potential difference between the reference electrode 205 and the gold electrode 213, the quantity of change of the potential difference between the reference electrode 205 and the gold electrode 213 during a certain period depends on the concentration of the measured substance. Accordingly, the concentration of the measured substance can be obtained by measuring the quantity of change of the potential difference before the injection of the sample solution or just after the injection of the sample solution and the potential difference at a predetermined time after the injection of the sample solution. Further, in a case where the reproducibility of the potential difference between the reference electrode 205 and the gold electrode 213 before the injection of the sample solution is higher than the accuracy required for the measurement, the concentration of the measured substance can be obtained by measuring the potential difference at a predetermined time after the injection of the sample solution.

In a case of measuring the oxidation reaction of the measured substance, it is preferred that the redox compound 209 is previously in an oxidized state. By providing the oxidized state the sensitivity at low concentration can be improved to extend the dynamic range. Alternatively, it is preferred that the ratio of the oxidation and reduction state is known for the redox compound 209 and the quantity in the reduced state is less than the quantity of the measured substance. For example, in a case where the concentration of the measured substance is 1 mM, it is set such that the concentration of the redox compound is 10 mM and oxidized state:reduced state=99:1 before the injection of the measured substance. After the injection of the measured substance, the redox compound ratio changes to oxidized state:reduced state=89:11 in accordance with the oxidation of the measured substance. The change of the ratio can be detected as the change of the surface potential in accordance with the Nernst's equation. In the same manner, in a case of measuring the reducing reaction of the measured substance, it is preferred that the redox compound 209 is previously in a reduced state. By providing the reduced state, the sensitivity at a low concentration can be improved to extend the dynamic range. Alternatively, it is preferred that the ratio of the oxidation and reduction state for the redox compound 209 is known and the quantity of the oxidized state is less than the quantity of the measured substance.

It is sometimes preferred that the redox compound 209 is a mixture of different kind of redox compounds. For example, while nicotinamide adenine dinucleotide (NAD) acts as an electron receptor in the oxidation reaction of cholesterol by a cholesterol dehydrogenase, ferricyan less act as an electron receptor in the reaction. On the other hand, in a case of using ferrocene for the redox compound 210 immobilized on the gold electrode 213, the redox reaction less occurs between ferrocene and NAD and it is difficult to measure the reduction of NAD as the change of potential. However, since redox reaction is taken place between ferrocene and ferricyan, reduction of ferricyan can be measured as the change of potential. In this case, by the use of a mixture of NAD and ferricyan as the redox compound 209, an equilibrium reaction is caused between NAD and ferricyan, and the reduction of NAD can be measured by way of reduction of ferricyan as the change of potential.

For the insulative molecules 211, an alkane thiol is used preferably. By the use of the alkane thiol, a highly insulative monolayer can be formed easily on the surface of a noble metal such as gold or silver. With a view point of the insulative property, the alkyl chain in the alkanethiol has a carbon chain of 6 or more.

The reference electrode 205 provides a reference potential for stably measuring the potential change based on an equilibrium reaction or chemical reaction occurring at the surface of the gold electrode 213 in the measuring solution 212. A silver chloride electrode or a calomel electrode using saturated potassium chloride as an internal solution is usually used as the reference electrode. A silver chloride electrode without an internal solution may be used as a quasi-reference electrode.

Instead of the gold electrode 213, an electrode comprising other noble metal such as silver or carbon may also be used.

A sample solution is not present in the measuring solution 212 before injection of the sample solution but a sample solution supplied from the sample solution injector 206 may function as such solution. In this case, the enzyme 208 and the redox compound 209 may be previously solidified by freeze drying or the like and dissolved by a sample solution supplied from the sample solution injector 206.

For oxidation and reduction of the measured substance by the enzyme 208, an enzyme for the pretreatment of the measured substance or a substrate needed for redox reaction may sometimes be used.

As the enzyme 208 in accordance with the measured substance, those exemplified in Table 2 can be used in addition to those exemplified in Table 1.

TABLE 2

| Target | Enzyme |
| --- | --- |
| Glucose | Glucose dehydrogenase |
| Cholesterol | Cholesterol dehydrogenase (for pretreatment: cholesterol esterase) |
| Lactate | Lactate dehydrogenase |
| Pyruvate | Pyruvate dehydrogenase (substrate: phosphoric acid) |
| Alcohol | Alcohol dehydrogenase |
| Triglyceride | Glycerol dehydrogenase (for pretreatment: Lipase) |

Figure 3:
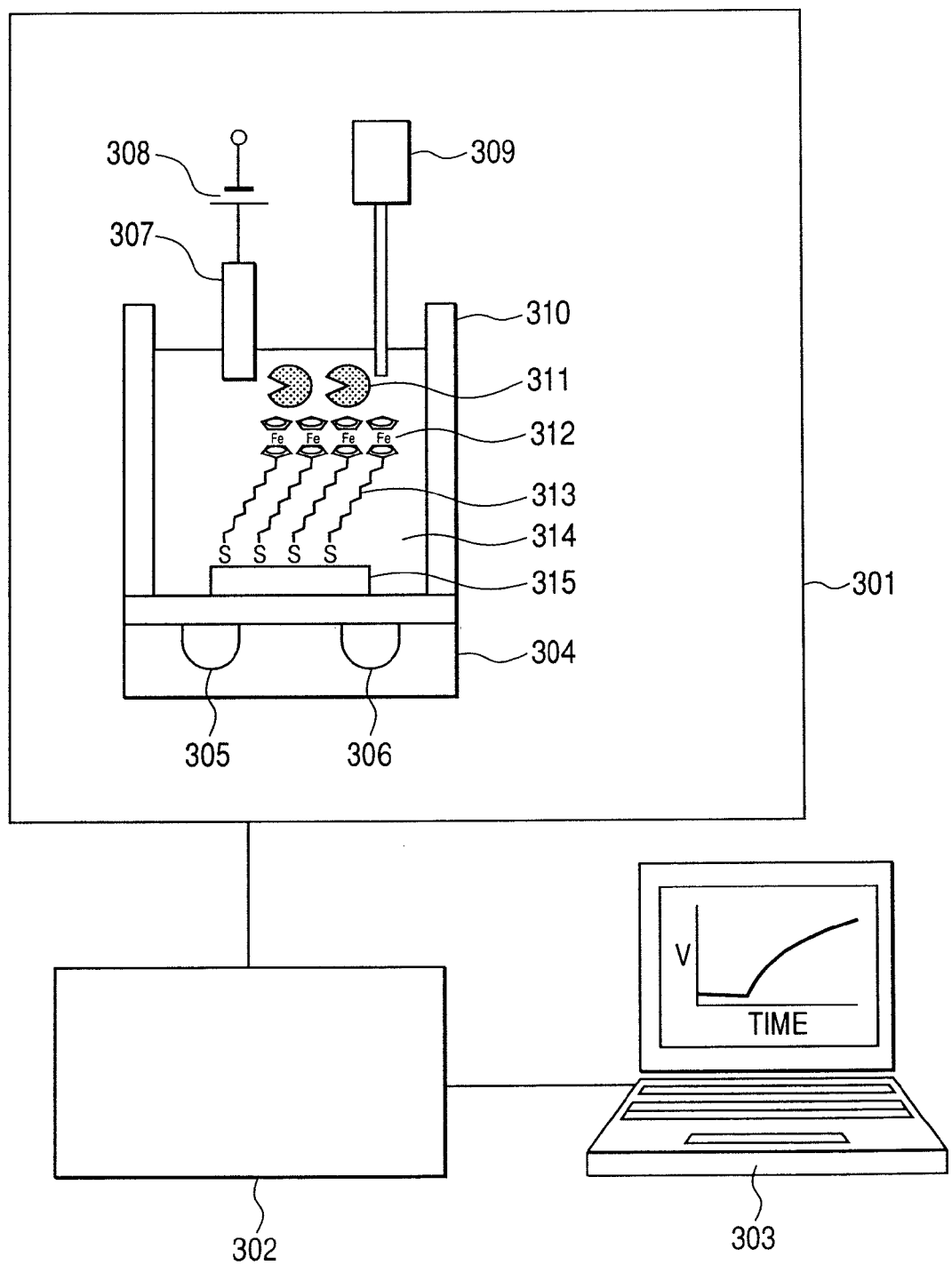
FIG. 3 is a block diagram showing an example of a potentiometric enzyme sensor using an FET sensor according to the invention.

FIG. 3 is a block diagram showing an example of a potentiometric enzyme sensor using an FET (Field Effect Transistor) sensor according to the invention. The measuring system of this embodiment includes a measuring station 301, a signal processing circuit 302, and a data processing apparatus 303. The measuring station 301 includes an insulated gate field-effect transistor 304, a reference electrode 307, a power source 308, a sample solution injector 309 for supplying a sample solution containing a measured substance, and a measuring cell 310. The insulated gate field-effect transistor 304 has a source 305, a drain 306, and a gold electrode 315 electrically connected with a gate. In a measuring solution 314 in the measuring cell 310, there are placed an enzyme 311, the gold electrode 315 on which a redox compound 312 is immobilized through insulative molecules 315, and the reference electrode 307. While an oxidase for oxidation and reduction is used as the enzyme, any enzyme that produces an oxidized substance or a reduced substance by an enzymatic reaction can be used with no trouble. For example, acetyl cholinesterase that hydrolyzes acetylthiocholin to produces a thiol compound, which is a reduced substance, can also be used.

The measuring procedures are as described below. A predetermined voltage is applied from the power source 308. A sample solution is injected by using the sample solution injector 309 into the measuring solution 314 in the measuring cell 310. The measured substance in the sample solution is oxidized by the enzymatic reaction and, along with the reaction, the dissolved oxygen in the sample solution is reduced to hydrogen peroxide. The produced hydrogen peroxide oxidizes the redox compound 312. As a result, the potential on the gold electrode 315 changes. A DC component of a current between the source 305 and the drain 306 in the insulated gate field-effect transistor 304 that changes before and after the injection of the sample solution by the sample solution injector 309 is measured at a real time and recorded by the signal processing circuit 302 and the data processing apparatus 303. The rate of change of the DC component of the current between the source 305 an the drain 306 depends on the potential on the gold electrode 315, and the potential on the gold electrode 315 depends on the rate of producing hydrogen peroxide, that is, the reaction rate of oxidation of the measured substance and the reaction rate of the oxidation of the measured substance depends on the concentration of the measured substance. Accordingly, the concentration of the measured substance can be obtained by measuring the rate of change of the DC component of the current between the source 305 and the drain 306.

Like the rate of change of the DC component of the current between the source 305 and the drain 306, the quantity of change of the DC component of the current between the source 305 and the drain 306 in a predetermined period depends on the concentration of the measured substance. Accordingly, the concentration of the measured substance can be obtained by measuring the quantity of change of the DC component of the current between the source 305 and the drain 306 before injection of the sample solution or just after the injection of the sample solution, and at a predetermined period after the injection of the sample solution. Further, in a case where the reproducibility of the DC component of the current between the source 305 and the drain 306 before injection of the sample solution is higher than the accuracy required for the measurement, the concentration of the measured substance can be obtained by measuring the DC component of the current between the source 305 and the drain 306 at a predetermined time after the injection of the sample solution.

It is preferred that the redox compound 312 is previously in a reduced state in a case of measuring an oxidation substance such as hydrogen peroxide. For providing the reduced state, the substance is treated with a reducing agent such as potassium ferrocyanide, sodium thiosulfate, or Dithiothreitol (DTT). By providing the reduced state, it is possible to stabilize the potential before the injection of the sample solution and, further, improve the sensitivity at a low concentration to extend a dynamic range. In the same manner, in a case of measuring a reducing substance such as a thiol compound, it is preferred that the substance is previously in an oxidized state. For providing an oxidized state, the substance is treated with an oxidizing agent such as potassium ferricyanide, potassium permanganate, or hydrogen peroxide. By applying the oxidizing treatment, it is possible to stabilize the potential before injection of the sample solution and, further, improve the sensitivity at a low concentration to extend a dynamic range.

In a case where the measured substance is oxidized or reduced by the enzyme 311 and, as a result, the oxidation and reduction state of the redox compound 312 changes, the oxidation and reduction state of the redox compound 312 may be changed by way of hydrogen peroxide as described above, by way of another redox compound as shown in FIG. 2, or directly by the oxidation reduction for the measured substance not by way of any redox compound.

For the insulative molecules 313, an alkanethiol is used preferably. By the use of the alkanethiol, a highly insulating monolayer can be formed easily on the surface of a noble metal such as gold or silver. With a view point of the insulative property, the alkyl chain in the alkanethiol has a carbon chain of 6 or more.

The reference electrode 307 provides a reference potential for stably measuring the potential change based on the equilibrium reaction or chemical reaction occurring at the surface of the gold electrode 315 in the measuring solution 314. A silver chloride electrode or calomel electrode using saturated potassium chloride as an internal solution is usually used as the reference electrode. A silver chloride electrode without an internal solution may be used as a quasi-reference electrode.

Instead of the gold electrode 315, an electrode formed of other noble metal such as silver may also be used.

A sample solution is not present in the measuring solution 314 before injection of the sample solution but a sample solution supplied from the sample solution injector 309 may function as such solution. In this case, the enzyme 311 may be previously solidified by freeze drying or the like and dissolved by a sample solution supplied from the sample solution injector 309.

The power source 308 is preferably a power source containing an AC component. By superimposing an AC voltage at 1 KHz or higher to the DC component, stabilization of the surface potential of the gold electrode 315 can be expected.

For oxidation and reduction of the measured substance by the enzyme 311, an enzyme for the pretreatment of the measured substance or a substrate needed for redox reaction may sometimes be used.

As the enzyme 311 in accordance with the measured substance, those exemplified in Table 1 and Table 2 can be used.

Figure 4:
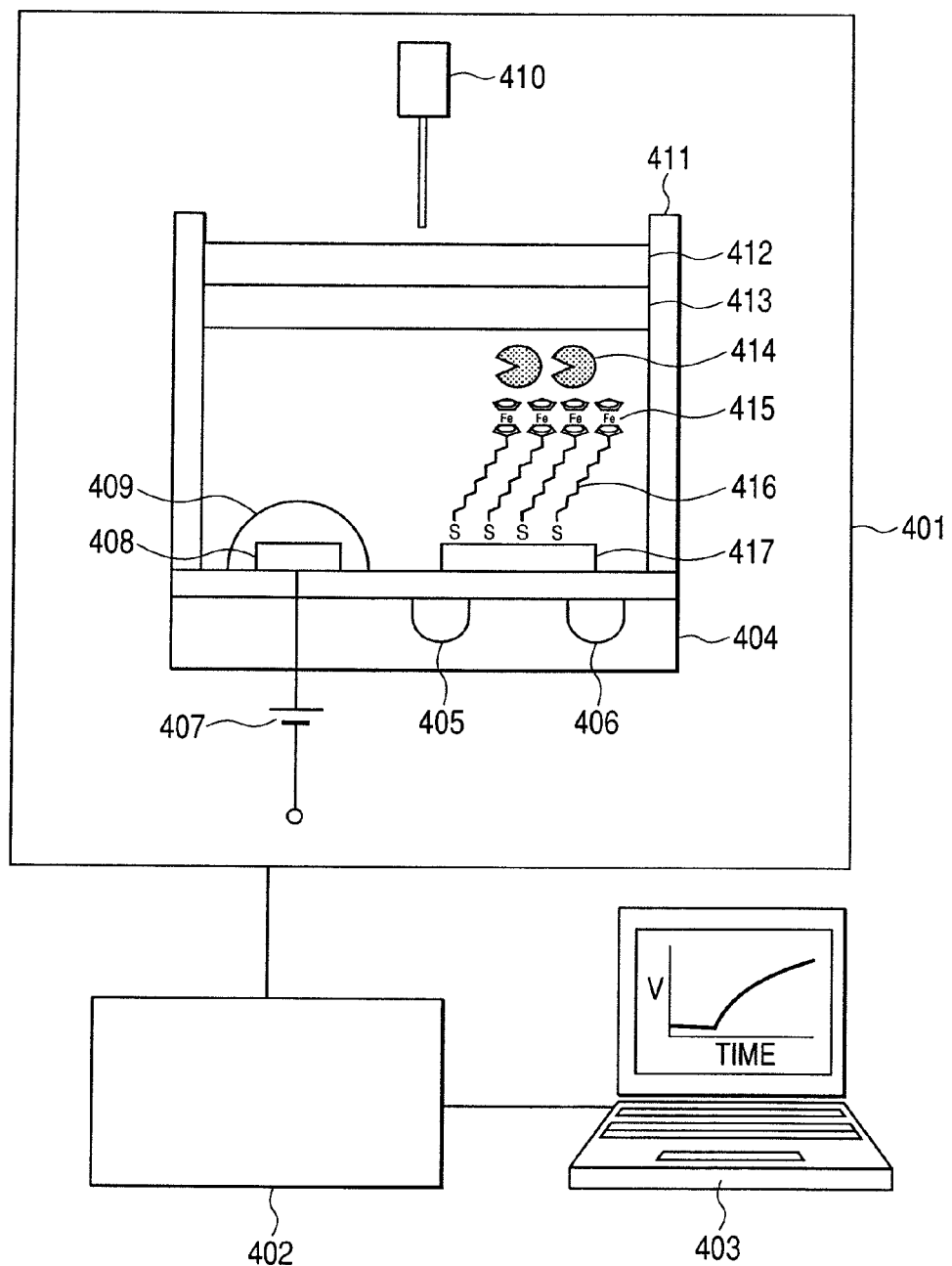
FIG. 4 is a block diagram showing an example of a potentiometric enzyme sensor using an FET sensor according to the invention.

FIG. 4 is a block diagram showing an example of a potentiometric enzyme sensor using an FET sensor according to the invention. The measuring system of this embodiment includes a measuring station 401, a signal processing circuit 402, and a data processing apparatus 403. The measuring station 401 includes an insulated gate field-effect transistor 404, a power source 407, a quasi-reference electrode 408, a sample solution injector 410 for supplying a sample solution containing a measured substance and a measuring cell 411. The insulated gate field-effect transistor 404 has a source 405, a drain 406, and a gold electrode 417 electrically connected with a gate. In the measuring cell 411, there are placed a blood cell separation membrane 412, a interfering substance separation membrane 413, an enzyme 414, a gold electrode 417 on which a redox compound 415 is immobilized through the insulative molecules 415, and the quasi-reference electrode 408, and a gel 409 containing a reference potential solution. While an oxidase for oxidation and reduction is used as the enzyme, any enzyme that produces an oxidized substance or a reduced substance by an enzymatic reaction can be used with no trouble. For example, acetyl cholinesterase that hydrolyzes acetylthiocholin to produces a thiol compound, which is a reduced substance, can also be used.

The measuring procedures are as described below. A predetermined voltage is applied from the power source 407. A sample solution such as a blood is injected by using the sample solution injector 410 in the measuring cell 411. The blood cell in the sample solution is removed by the blood cell separation membrane 412 and interfering substances giving an effect on the surface potential of ascorbic acid, etc. in the sample solution are removed by the interfering substance separation membrane 413. The liquid permeating the separation membranes dissolves the enzyme 414. The measured substance in the sample solution is oxidized by the enzymatic reaction and, along with the reaction, dissolved oxygen in the sample solution is reduced to hydrogen peroxide. The produced hydrogen peroxide oxidizes the redox compound 415. As a result, the potential on the gold electrode 417 changes. A DC component of a current between the source 405 and the drain 406 in the insulated gate field-effect transistor 404 is measured at a real time and recorded by the signal processing circuit 402 and the data processing apparatus 403. The rate of change of the DC component of the current between the source 405 and the drain 406 depends on the potential of the gold electrode 417, and the potential on the gold electrode 417 depends on the rate of producing hydrogen peroxide, that is, the reaction rate of oxidation of the measured substance and the reaction rate of the oxidation of the measured substance depends on the concentration of the measured substance. Accordingly, the concentration of the measured substance can be obtained by measuring the rate of change of the DC component of the current between the source 405 and the drain 406.

In a case of using urine as the sample solution, the urine is preferably diluted and injected into the measuring cell 411 by using the sample solution injector 410. In this case, the blood cell separation membrane 412 is no more necessary but, instead, a protein removing membrane is used preferably.

Like the rate of change of the DC component of the current between the source 405 and the drain 406, the quantity of change of the DC component of the current between the source 405 and the drain 406 in a predetermined period depends on the concentration of the measured substance. Accordingly, the concentration of the measured substance can be obtained by measuring the quantity of change of the DC component of the current between the source 405 and the drain 406 before injection of the sample solution or just after the injection of the sample solution and at a predetermined period after the injection of the sample solution. Further, in a case where the reproducibility for the DC component of the current between the source 405 and the drain 406 before injection of the sample solution is higher than the accuracy required for the measurement, the concentration of the measured substance can be obtained by measuring the DC component of the current between the source 405 and the drain 406 at a predetermined time after the injection of the sample solution.

It is preferred that the redox compound 415 is previously in a reduced state in a case of measuring an oxidation substance such as hydrogen peroxide. For providing the reduced state, the substance is treated with a reducing agent such as potassium ferrocyanide, sodium thiosulfate, or Dithiothreitol (DTT). By providing the reduced state, it is possible to stabilize the potential before the injection of the sample solution and, further, improve the sensitivity at a low concentration to extend a dynamic range. In the same manner, in a case of measuring a reducing substance such as a thiol compound, it is preferred that the substance is previously in an oxidized state. For providing an oxidized state, the substance is treated with an oxidizing agent such as potassium ferricyanide, potassium permanganate, or hydrogen peroxide. By applying the oxidizing treatment, it is possible to stabilize the potential before injection of the sample solution and, further, improve the sensitivity at a low concentration to extend a dynamic range.

In a case where the measured substance is oxidized or reduced by the action of the enzyme 414 and, as a result, the oxidation and reduction state of the redox compound 415 changes, the oxidation and reduction state of the redox compound of the redox compound 415 may be changed by way of hydrogen peroxide as described above, by way of another redox compound as shown in FIG. 2, or directly by the oxidation reduction for the measured substance not by way of any redox compound.

For the insulative molecules 416, an alkane thiol is used preferably. By the use of the alkane thiol, a highly insulating monolayer can be formed easily on the surface of a noble metal such as gold or silver. With a view point of an insulative property, the alkyl chain in the alkanethiol has a carbon chain of 6 or more.

For the quasi-reference electrode 408, a silver chloride electrode or an electrode coated with a silver/silver chloride paste is preferred. Further, the entire apparatus can be made smaller by forming the field-effect transistor 404 and the quasi-reference electrode 408 on one identical substrate. The gel 409 containing a solution for reference voltage is used for keeping the fluctuation of the potential of the quasi-reference electrode 408 smaller than the accuracy required for measurement during measurement. For example, in a case of using the silver-silver chloride electrode for the quasi-reference electrode 408, a gel containing an aqueous solution of potassium chloride is used preferably. Further, instead of the gel 409 containing the solution for reference voltage, a hydrophilic fluoro resin film or a porous film can be used. In a case where the fluctuation of the potential of the quasi-reference electrode 408 is less than the accuracy required for the measurement without using the gel 409 containing the solution for reference voltage, such gel 409 containing the solution for reference potential may not be used.

Instead of the gold electrode 417, an electrode comprising other noble metal such as silver may also be used.

The power source 407 is preferably a power source containing an AC component. By superimposing an AC voltage at 1 KHz or higher to the DC component, stabilization of the surface potential of the gold electrode 417 can be expected.

For oxidation and reduction of the measured substance by the enzyme 414, an enzyme for the pretreatment of the measured substance or a substrate needed for redox reaction may sometimes be used.

As the enzyme 414 in accordance with the measured substance, those exemplified in Table 1 and Table 2 can be used.

Figure 5:
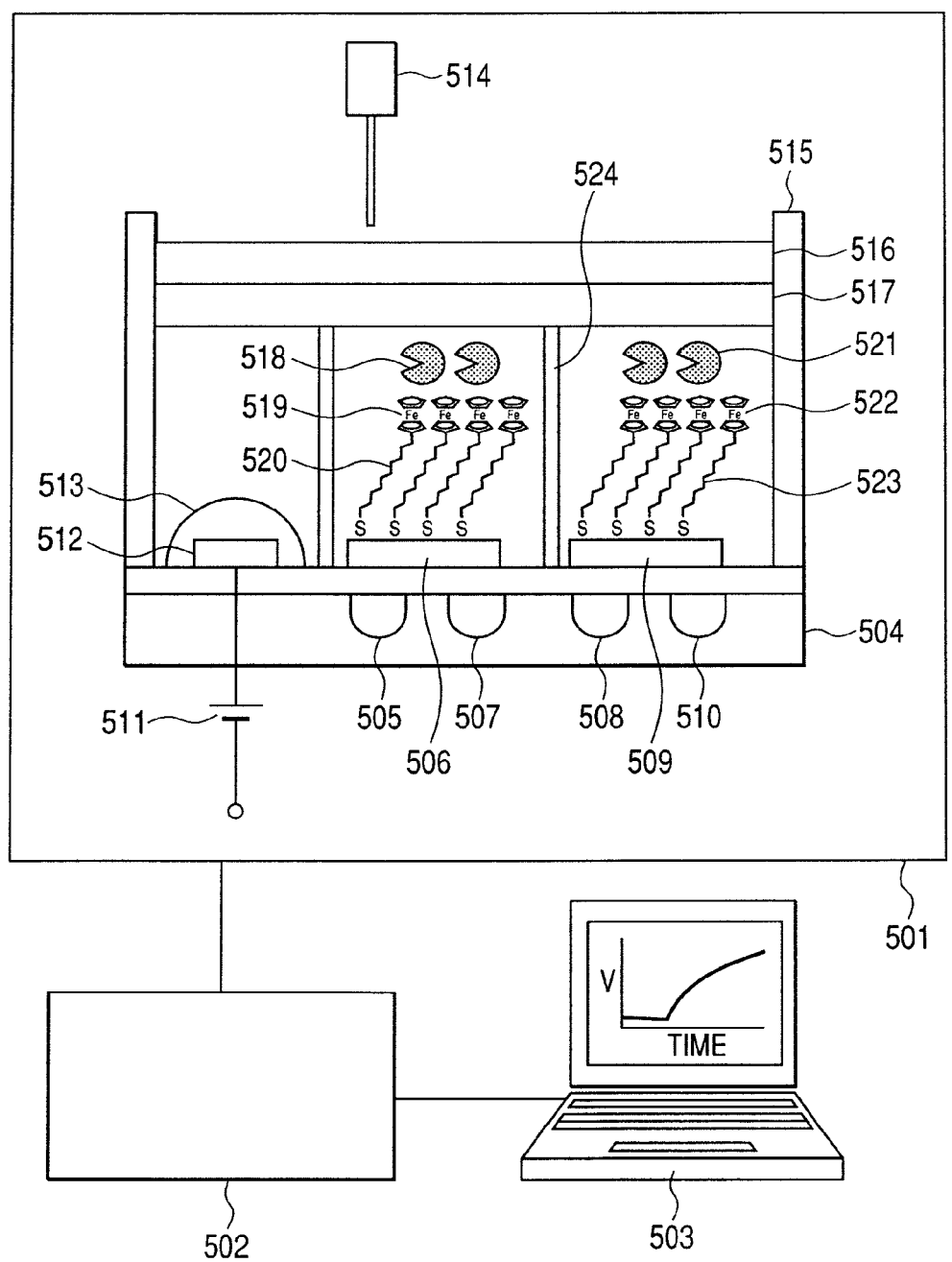
FIG. 5 is a block diagram showing an example of a potentiometric enzyme sensor using an EFT sensor according to the invention capable of measuring plural targets together.

FIG. 5 is a block diagram showing an example of a potentiometric enzyme sensor using an FET sensor according to the invention capable of measuring plural targets simultaneously. The measuring system of this embodiment includes a measuring station 501, a signal processing circuit 502, and a data processing apparatus 503. The measuring station 501 includes an insulated gate field-effect transistor 504, a quasi-reference electrode 512, a sample solution injector 514 for supplying a sample solution containing a measured substance and a measuring cell 515. The insulated gate field-effect transistor 504 has a plurality of combinations each comprising a source 505, a drain 507, a gold electrode 506 electrically connected with the gate, and a source 508, a drain 510, and a gold electrode 509 electrically connected with the gate. In the measuring cell 515, there are placed a blood cell separation membrane 516, a interfering substances separation membrane 517, the quasi-reference electrode 512, and a gel 513 containing a solution for reference potential, and an enzyme 518 and a redox compound 519 immobilized through insulative molecules 520 to the gold electrode 506, and an enzyme 521, and a redox compound 522 immobilized through an insulative molecules 523 to the gold electrode 509, corresponding to the respective gold electrodes 506, 509. The respective gold electrodes 506, 509, the enzymes 518, 521, and the redox compounds 519, 521 immobilized to the gold electrodes 506, 509 through the insulative molecules 520, 523 are separated by a separation wall 524. In this case, while an oxidase for oxidation and reduction is used as the enzyme, any enzyme that produces an oxidized substance or a reduced substance by an enzymatic reaction can be used with no trouble. For example, acetyl cholinesterase that hydrolyzes acetylthiocholin to produce a thiol compound, which is a reduced substance, can also be used.

The measuring procedures are as described below. A predetermined voltage is applied from the power source 511. A sample solution such as a blood is injected by using a sample solution injector 514 in the measuring cell 515. Blood cells in the sample solution are removed by the blood cell separation membrane 516 and interfering substances giving an effect on the surface potential such as ascorbic acid in the sample solution are removed by the interfering substances separation membrane 517. The liquid permeating the separation membranes dissolves the enzymes 518, 521. The measured substance in the sample solution is oxidized by the enzymatic reaction and, along with the reaction, the dissolved oxygen in the sample solution is reduced to hydrogen peroxide. The hydrogen peroxide produced by the enzyme 518, 521 oxidizes the redox compounds 519, 522. As a result, the potentials on the gold electrodes 506, 509 are changed. The DC component of the current between the source 505 and the drain 507, and between the source 508 and the drain 510 in the insulated gate field-effect transistor 504 is measured at a real time and recorded by the signal processing circuit 502 and the data processing apparatus 503. The rate of change of the DC component of the current between the source 505 and the drain 507 depends on the potential of the gold electrode 506, the potential of the gold electrode 506 depends on the rate of producing hydrogen peroxide, that is, the reaction rate of oxidation of the measured substance corresponding to the enzyme 518, and the reaction rate of the oxidation of the measured substance depends on the concentration of the measured substance. Accordingly, by measuring the rate of change of the DC component of the current between the source 505 and the drain 507, a concentration of the measured substance corresponding to the enzyme 518 can be obtained. In the same manner, the concentration of the measured substance corresponding to the enzyme 521 can be obtained by measuring the rate of change of the DC component of the current between the source 508 and the drain 510.

In a case of using urine as the sample solution, the urine is preferably diluted and injected into the measuring cell 515 by using the sample solution injector 514. In this case, the blood cell separation membrane 516 is no more necessary but, instead, a protein removing membrane is used preferably.

The separation wall 524 serves to prevent dissolved enzymes 518 and 521 from mixing to each other and not to cause cross talk. As the separation membrane 524, a hydrophilic fluoro resin film or a porous film is used preferably. An identical effect can be obtained also by immobilizing the enzyme on a polymeric film and disposing the polymeric film on the redox compound instead of using the separation wall.

It is preferred that the redox compounds 519, 522 are previously in a reduced state in a case of measuring an oxidation substance such hydrogen peroxide. For providing the reduced state, the substance is treated with a reducing agent such as potassium ferrocyanide, sodium thiosulfate, or Dithiothreitol (DTT). By providing the reduced state, it is possible to stabilize the potential before the injection of the sample solution and, further, improve the sensitivity at a low concentration to extend a dynamic range. In the same manner, in a case of measuring a reducing substance such as a thiol compound, it is preferred that the substance is previously in an oxidized state. For providing an oxidized state, the substance is treated with an oxidizing agent such as potassium ferricyanide, potassium permanganate, or hydrogen peroxide. By applying the oxidizing treatment, it is possible to stabilize the potential before injection of the sample solution and, further, improve the sensitivity at a low concentration to extend a dynamic range.

In a case where the measured substance is oxidized or reduced by the action of the enzyme 518, 521 and, as a result, the oxidation and reduction state of the redox compound 519, 522 changes, the oxidation and reduction state of the redox compound of the redox compound 519, 522 may be changed by way of hydrogen peroxide as described above, by way of another redox compound as shown in FIG. 2, or directly by the oxidation reduction for the measured substance not by way of any redox compound.

For the insulative molecules 520, 523, an alkanethiol is used preferably. By the use of the alkanethiol, a highly insulating monolayer can be formed easily on the surface of a noble metal such as gold or silver. With a view point of an insulative property, the alkyl chain in the alkanethiol has a carbon chain of 6 or more.

For the quasi-reference electrode 512, a silver chloride electrode or an electrode coated with a silver/silver chloride paste is preferred. Further, the entire apparatus can be made smaller by forming the field-effect transistor 504 and the quasi-reference electrode 512 on one identical substrate. The gel 513 containing a solution for reference voltage is used for keeping the fluctuation of the potential of the quasi-reference electrode 512 less than the accuracy required for measurement during measurement. For example, in a case of using the silver-silver chloride electrode for the quasi-reference electrode 512, a gel containing an aqueous solution of potassium chloride is used preferably. Further, instead of the gel 513 containing the solution for reference voltage, a hydrophilic fluoro resin film or a porous film can be used. In a case where the fluctuation of the potential of the quasi-reference electrode 512 is less than the accuracy required for the measurement without using the gel 513 containing the solution for reference voltage, such gel 513 containing the solution for reference potential may not be used.

Instead of the gold electrodes 506, 509, an electrode comprising other noble metal such as silver may also be used.

The power source 511 is preferably a power source containing an AC component. By superimposing an AC voltage at 1 KHz or higher to the DC component, stabilization of the surface potential of the gold electrodes 506, 509 can be expected.

For oxidation and reduction of the measured substance by the enzymes 518, 521, an enzyme for the pretreatment of the measured substance or a substrate needed for redox reaction may sometimes be used.

As the enzymes 518, 521 in accordance with the measured substance, those exemplified in Table 1 and Table 2 can be used.

In this embodiment, an apparatus having two sets of enzymes, gold electrodes, etc. capable of measuring two targets simultaneously has been described but an apparatus capable of measuring more than three targets simultaneously can also be constructed in the same manner.

Figure 6A:
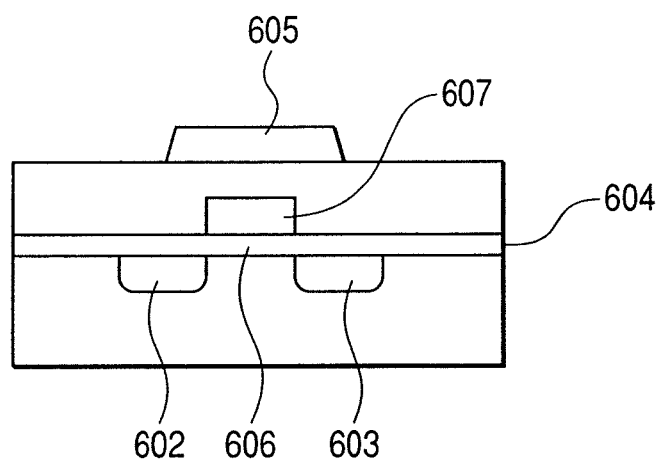
FIG. 6 is a view showing an example of an analytical element used for a potentiometric enzyme sensor using an FET sensor according to the invention.
Figure 6B:
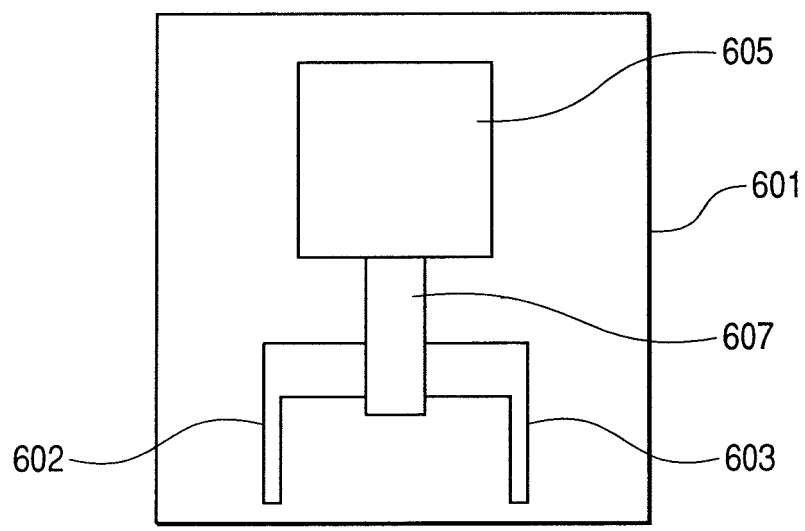

FIG. 6 is a view showing an example of a structure for an analytical element used in a potentiometric enzyme sensor using an FET sensor according to the invention. FIGS. 6A and 6B respectively show a cross sectional structure and a planer structure. In an insulated gate field-effect transistor 601, a source 602, a drain 603, and a gate insulator 604 are formed on the surface of a silicon substrate, and a gold electrode 605 is arranged. The gold electrode 605 and the gate 606 of the insulated gate field-effect transistor are connected through a conductive wiring 607. The insulated gate field-effect transistor is, preferably, a metal-oxide semiconductor field-effect transistor using a silicon oxide as an insulative film, but a thin film transistor (TFT) may also be used with no problem. By adopting this structure, the gold electrode 605 can be formed at an arbitrary place to an arbitrary size, and the capacity of the measuring cell can be varied in accordance with the amount of the sample solution as a measured substance. The insulated gate field-effect transistor used in the invention is a depletion type FET having an insulation layer using $SiO_2$ (thickness: 17.5 nm) and the gold electrode is prepared to a size of 400 μm×400 μm. Since an aqueous solution is used for the usual measurement, the device has to operate in a solution. In a case of measurement in the solution, it is necessary that the device operates in an electrode potential range from −0.5 to 0.5 V causing less electrochemical reaction. For this purpose, in this embodiment, the threshold voltage of FET is set to about −0.5V by controlling parameters for manufacturing the depletion type n-channel FET, that is, the parameters for ion implantation to control the threshold voltage (Vt). Instead of the gold electrode, an electrode comprising other noble metal such as silver may also be used. A device having two or more YET sensors on one identical substrate is prepared by forming the FET sensor in FIG. 6 in plurality on one identical substrate. Cross talk between the FET sensors causing a problem in this case can be mitigated by adopting an SOI (Silicon on Insulator) structure.

Figure 7A:
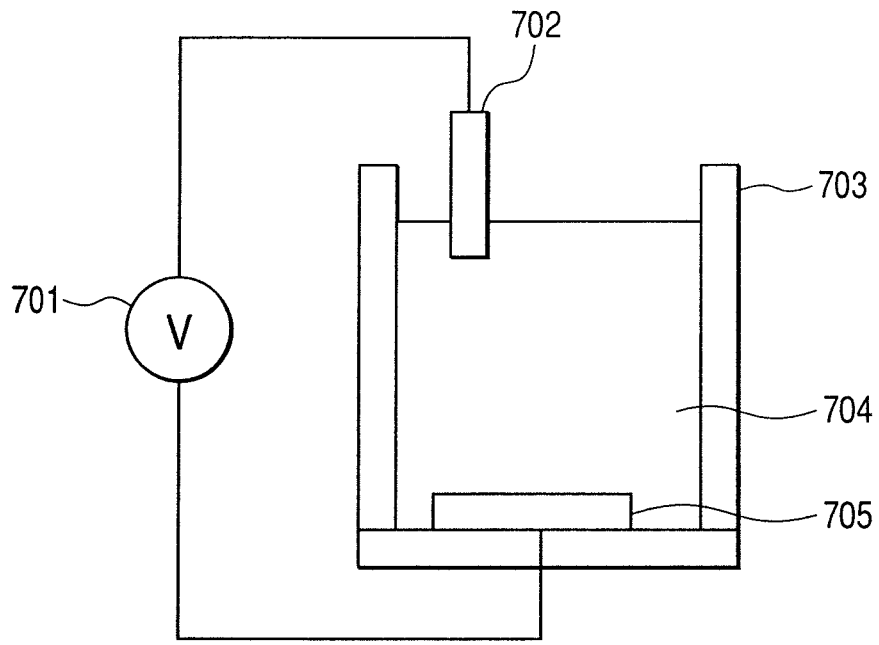
FIG. 7 is an explanatory view for an evaluation system of immobilizing a redox compound through insulative molecules on the surface of a working electrode.
Figure 7B:
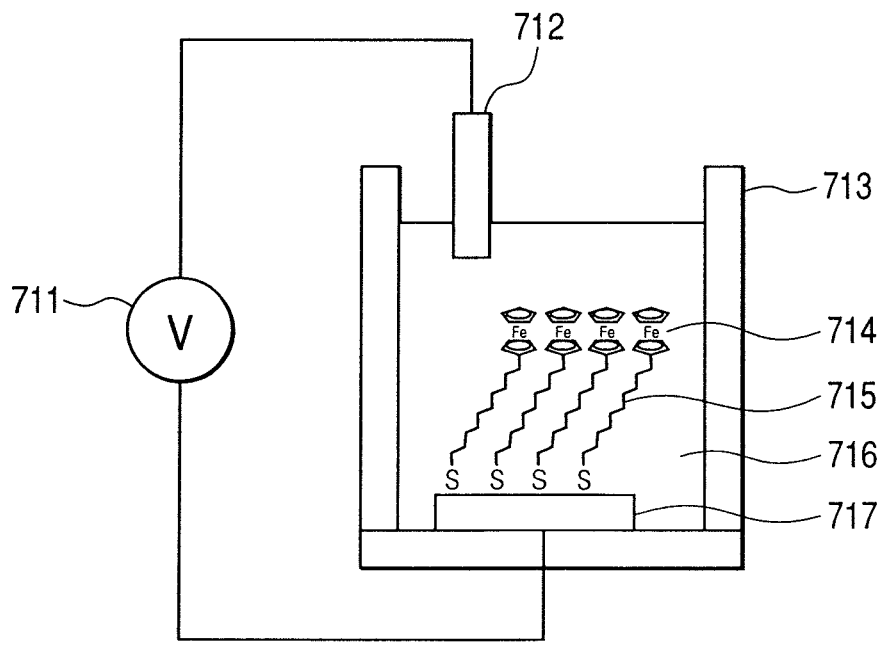

The effect of immobilizing the redox compound on the surface of the working electrode through the insulative molecules according to the invention is to be described with reference to other example. FIG. 7A shows an evaluation system in a case of using an unmodified working electrode and FIG. 7B shows an evaluation system in a case of immobilizing a redox compound to the surface of a working electrode through insulative molecules. The evaluation system in a case of using the unmodified working electrode includes a potentiometric measuring device 701, a reference electrode 702, and a measuring cell 703. In the measuring cell 703, there are placed a measuring solution 704, a gold electrode 705, and a reference electrode 702. The evaluation system in a case of immobilizing a redox compound through insulative molecules to the surface of a working electrode includes a potentiometric measuring device 711, a reference electrode 712, and a measuring cell 713. In the measuring cell 713, there are placed a measuring solution 716, a gold electrode 717 in which a redox compound 714 is immobilized through insulative molecules 715, and the reference electrode 712.

Figure 8:
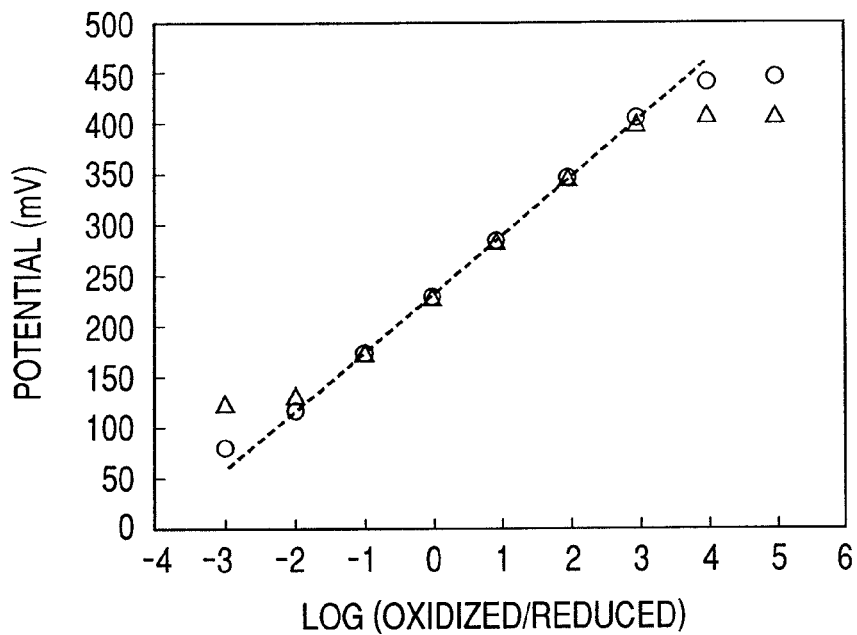
FIG. 8 is a graph showing the effect of immobilizing a redox compound through insulative molecules on the surface of a working electrode.

FIG. 8 shows a potential difference between the reference electrode and the gold electrode against the logarithm of a redox compound concentration ratio in the measuring solution (logarithm for the ratio of potassium ferricyanide concentration and potassium ferrocyanide concentration). In FIG. 8, open triangles (A) show the result of measurement using the evaluation system of FIG. 7A and open circles in FIG. 8 shows the result of measurement using the evaluation system of FIG. 7B. For the reference electrodes 702, 712, a silver chloride reference electrode using an aqueous solution of saturated potassium chloride as the internal solution is used. For the redox compound 714 immobilized through insulative molecules 715, 11-ferrocenyl-1-undecanethiol (11-FUT) was used. For the measuring solutions 704, 716, a 0.1M aqueous solution of sodium sulfate containing potassium ferricyanide and potassium ferrocyanide at a total concentration of 10 μM was used. The measuring temperature was 25° C. Within a range of the logarithm of the redox compound concentration ratio from −1 to 3, both the open triangles and the open circles can be well fitted with a line of 58 mV/decade and it can be seen that the potential is generated in accordance with the Nernst's equation. However, the open triangles deviate from the line at the logarithm for the redox compound concentration ratio of −2 or less or 4 or more and the range of the potential fitted with the line is 134 to 409 mV, which corresponds to the concentration range of 4.7 digits. On the other hand, for the open circles, the range of the voltage fitted with the line is from 80 to 442 mV, which corresponds to the concentration range of 6.2 digits. That is, by immobilizing the redox compound through the insulative molecules on the surface of the working electrode, the dynamic range was improved by 1.5 digits.

Without immobilization of the insulative molecules to the surface of the working electrode, the insulative property between the working electrode and the measuring solution is low. Accordingly, due to the effect of the leak current on the electrode surface, minute change of the concentration of the measured substance cannot be detected. On the other hand, by immobilizing the redox compound through the insulative molecules on the surface of the working electrode, insulative property between the working electrode and the measuring solution is increased to decrease the leak current on the surface of the electrode, and a further minute change of the measured substance can be detected. In this case, by immobilizing the redox compound through the insulative molecules of an identical length on the surface of the working electrode, the working electrode can obtain insulative property and change of state of the immobilized redox compound can give an effect on the surface potential of the working electrode uniformly.

Figure 9:
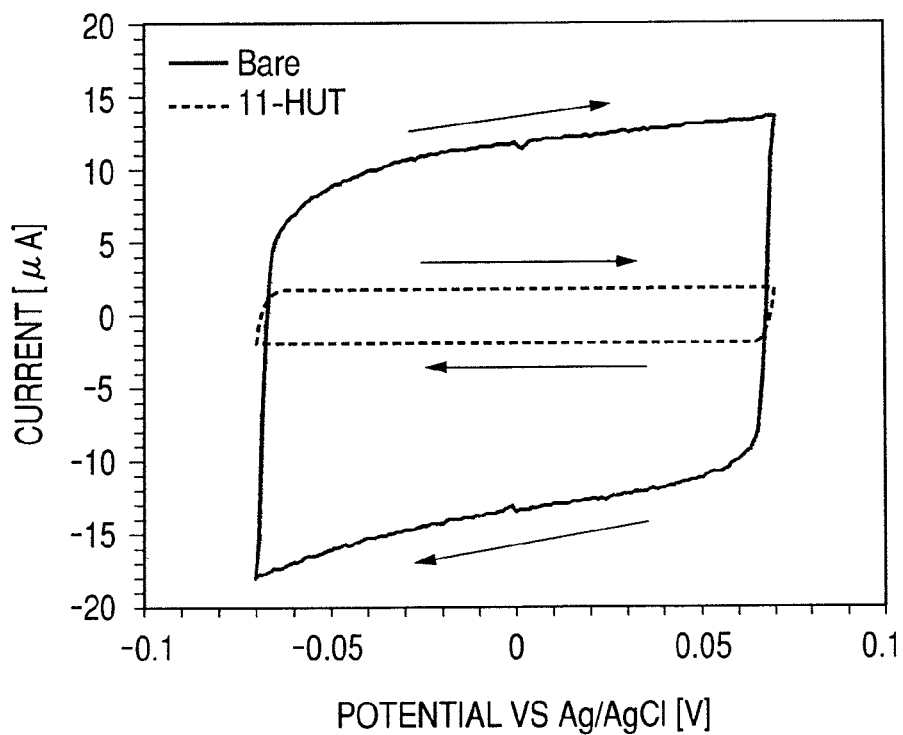
FIG. 9 is a graph showing the effect of immobilizing a redox compound through insulative molecules on the surface of a working electrode.

The effect of immobilizing the redox compound through the insulative molecules to the surface of the working electrode in the invention is to be described with reference to other embodiment. FIG. 9 shows voltammograms of a gold electrode in which an unmodified gold electrode and insulative molecules are immobilized. For the potentiostat, an electrochemical analyzer ALS Model 611B was used. As the reference electrode, a silver chloride reference electrode using a saturated aqueous solution of potassium chloride as the internal solution is used. As the counter electrode, a platinum wire was used. As the solution, a 0.1 M aqueous solution of sodium sulfate is used. In the voltamogram, the difference of current value depending on the sweeping direction shows the capacitance of the surface of the electrode and the slope of the current value against the applied potential shows the resistance of the electrode surface. Compared with the unmodified gold electrode, in a gold electrode on which 11-hydroxy-1-hexanthiol (11-HUT) was immobilized as the insulative molecules, the slope of the current value against the application potential was small. This means that the insulative property at the surface of the electrode is increased by immobilization of the insulative molecules on the electrode surface. Further, compared with the unmodified gold electrode, in the gold electrode immobilizing 11-HUT as the insulative molecules, the absolute value of the current was small. This is because a layer of about one molecule referred to as an electric double layer is present on the surface of the electrode in the unmodified gold electrode and the surface has such a large capacitance as 14 µF/cm$^2$, whereas the insulative molecules are immobilized to the electrode surface thereby forming an insulation layer of about 2 nm as the length of insulative molecules, and the capacitance is reduced to 2.3 µF/cm$^2$. By immobilizing the insulative molecules to the surface of the electrode, the resistance value on the surface of the electrode is increased and the capacitance is decreased. As a result, the leak current is decreased and, further, charging current is also decreased, so that further miner change of the concentration of the redox compound can be recognized.

Figure 10:
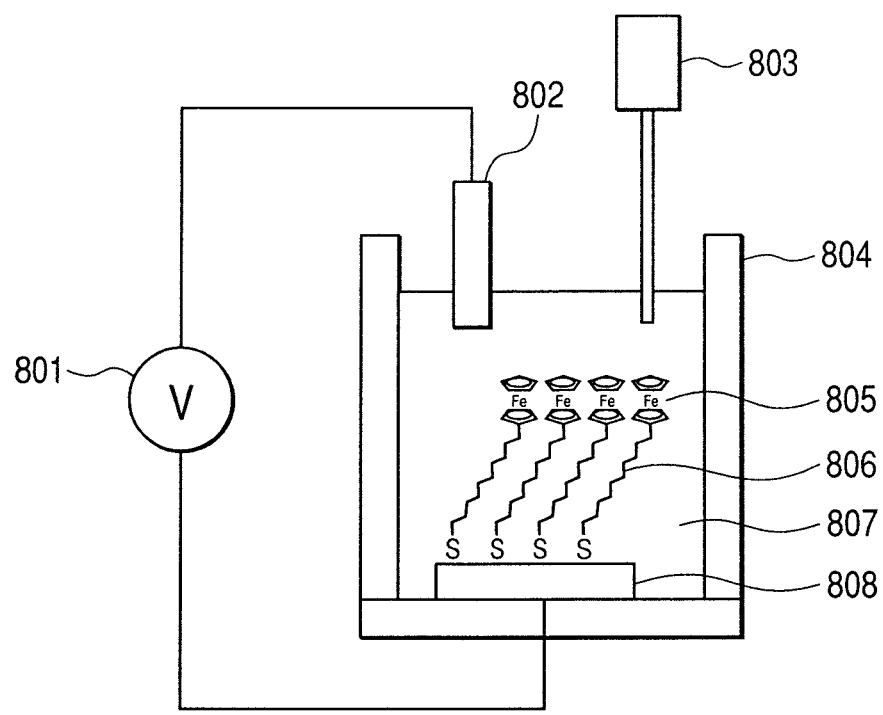
FIG. 10 is an explanatory view for an evaluation system of immobilizing a redox compound through insulative molecules on the surface of a working electrode.

The effect of immobilizing the redox compound through the insulative molecules on the surface of the working electrode according to the invention is to be described with reference to other example. FIG. 10 shows an evaluation system in a case of immobilizing the redox compound through insulative molecules on the surface of the working electrode. The evaluation system includes a potentiometric device 801, a reference electrode 802, a sample solution injector 803 for supplying a sample solution containing measured substance, and a measuring cell 804. In the measuring solution 807 in the measuring cell 804, a gold electrode 808 and a reference electrode 802 on which the redox compound 805 is immobilized through insulative molecules 806 are arranged.

Figure 11:
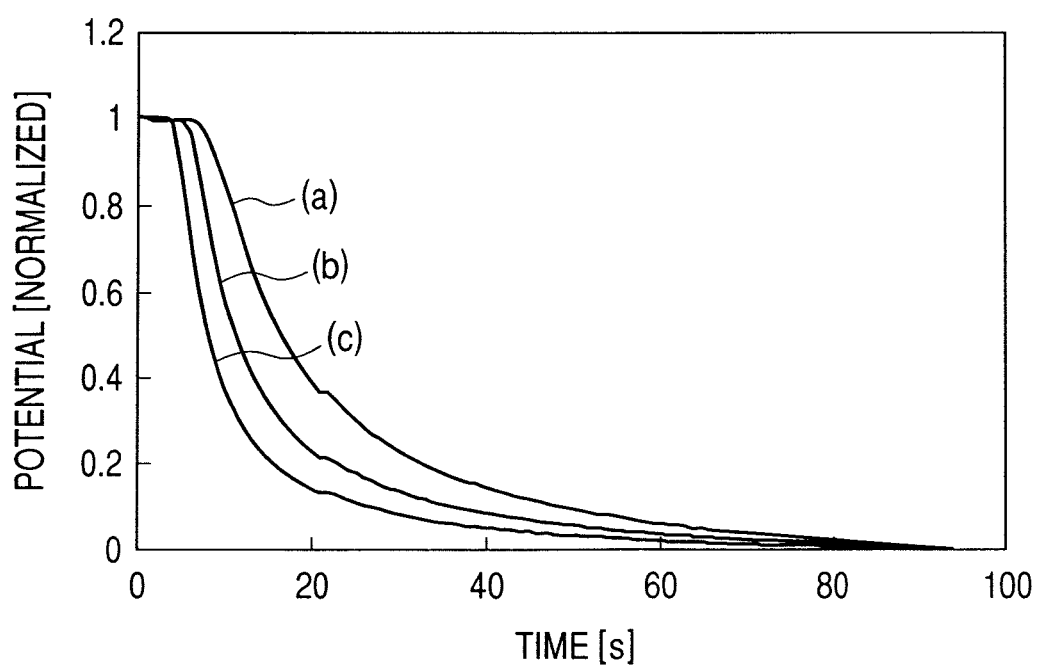
FIG. 11 is a graph showing the effect of immobilizing a redox compound through insulative molecules on the surface of a working electrode.

FIG. 11 shows the time course of the potential difference between the reference electrode and the gold electrode upon injecting a measured substance. For the reference electrode 802, a silver chloride reference electrode using an saturated aqueous solution of potassium chloride as the internal solution is used. For the redox compound 805 immobilized through the insulative molecules 806, (a) 6-ferrocenyl-1-hexanethiol, (b) 8-ferrocenyl-octanethiol, and (c) 11-FUT are used. For the sample solution in the sample solution injector, an aqueous solution of potassium ferrocyanide was used. For the measuring solution 807, a 0.1M aqueous solution of sodium sulfate was used. The abscissa in FIG. 11 shows the time with the instance of sample injection as 0, and the ordinate shows the potential between the reference electrode and the gold electrode which is normalized with the potential just before the injection of the sample solution as 1 and the potential 100 sec after the injection as 0. Assuming the time till the potential changes to 0.1 by the injection of the sample solution, that is, the time required for the 90% potential change as a relaxation time, the relaxation time was in the order of (a)>(b)>(c). That is, as the length of the insulative molecules 806 is longer, the relaxation time was shorter. As the length of the insulative molecules 806 is longer, the insulative property between the working electrode and the measuring solution is higher. That is, as the insulative property is higher, the response speed is faster.

Figure 12:
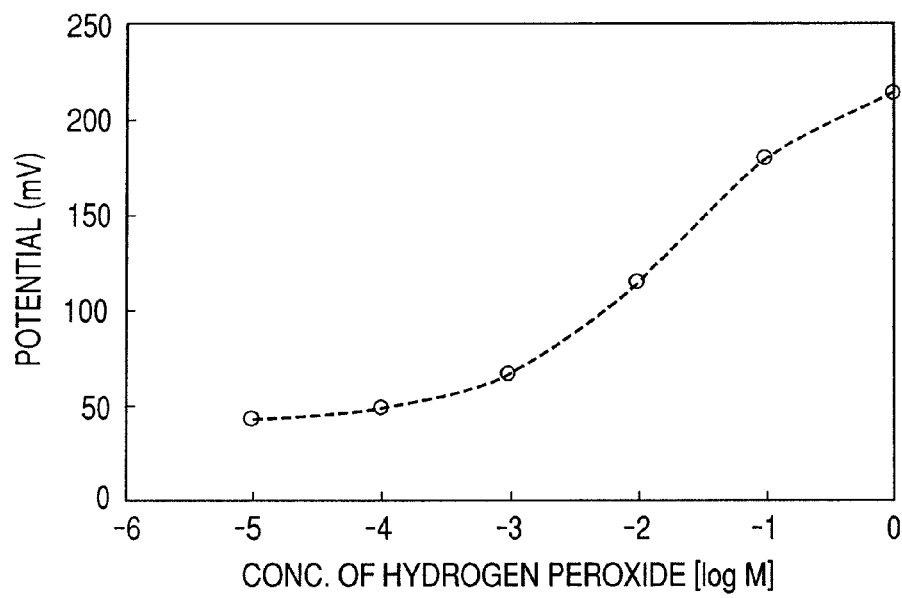
FIG. 12 is a graph showing the result of measuring hydrogen peroxide using a working electrode on which a redox compound is immobilized through insulative molecules.

FIG. 12 shows the result of measuring hydrogen peroxide by using a potentiometric sensor in which the redox compound is immobilized through the insulative molecules on the working electrode according to the invention. In this example, measurement is conducted by the constitution of the apparatus shown in FIG. 7B. 11-FUT was used for the redox compound immobilized through the insulative molecules on the gold electrode, a 0.1M aqueous solution of sodium sulfate is used for the measuring solution, and a silver chloride electrode using saturated potassium chloride as the internal solution is used for the reference electrode. The abscissa in FIG. 12 shows the concentration of hydrogen peroxide and the ordinate represents the potential. This result shows that a potential in accordance with the concentration of hydrogen peroxide is generated. This is because the redox compound immobilized on the surface of the gold electrode is oxidized by hydrogen peroxide.

Figure 13:
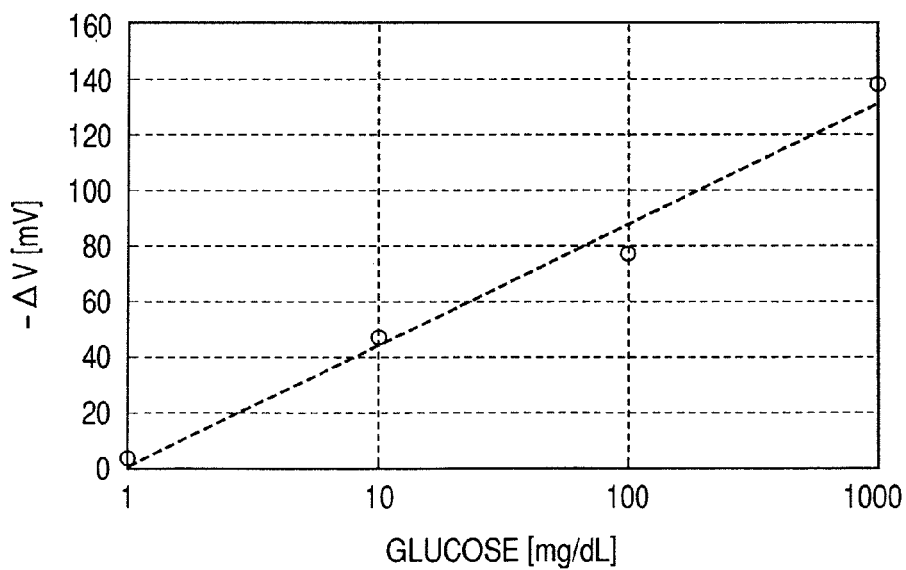
FIG. 13 is a graph showing the result of measuring glucose concentration by using a potentiometric enzyme sensor according to the invention.

FIG. 13 shows the result of measuring a glucose concentration by using the potentiometric enzyme sensor according to the invention. In this embodiment, measurement was conducted by the constitution of the apparatus shown in FIG. 2. Generally, in a case where glucose is at a high concentration, since the concentration of dissolved oxygen in the blood (partial pressure) is insufficient to restrict the reaction, potassium ferricyanide is used as another redox compound instead of oxygen. 11-FUT is used for the redox compound immobilized through the insulative molecules, a 0.1M phosphate buffer solution (PBS) at pH 7.4 is used for the measuring solution, a glucose oxidase was used as the enzyme, potassium ferrocyanide was used as a water soluble redox compound, and a silver chloride electrode using saturated potassium chloride as the internal solution is used for the reference electrode. Aqueous solutions of glucose at 1, 10, 100, 1,000 mg/dl are used for the sample solution. The abscissa shows a glucose concentration and the ordinate shows a potential difference before injection and 100 sec after the injection of the measured substance. This result shows that a potential in accordance with the glucose concentration is generated. This is because the reaction of glucose and potassium ferricyanide catalyzed by the glucose oxidase produces gluconolactone and potassium ferrocyanide, and ferrocene immobilized on the gold electrode is reduced by produced potassium ferrocyanide.

Figure 14:
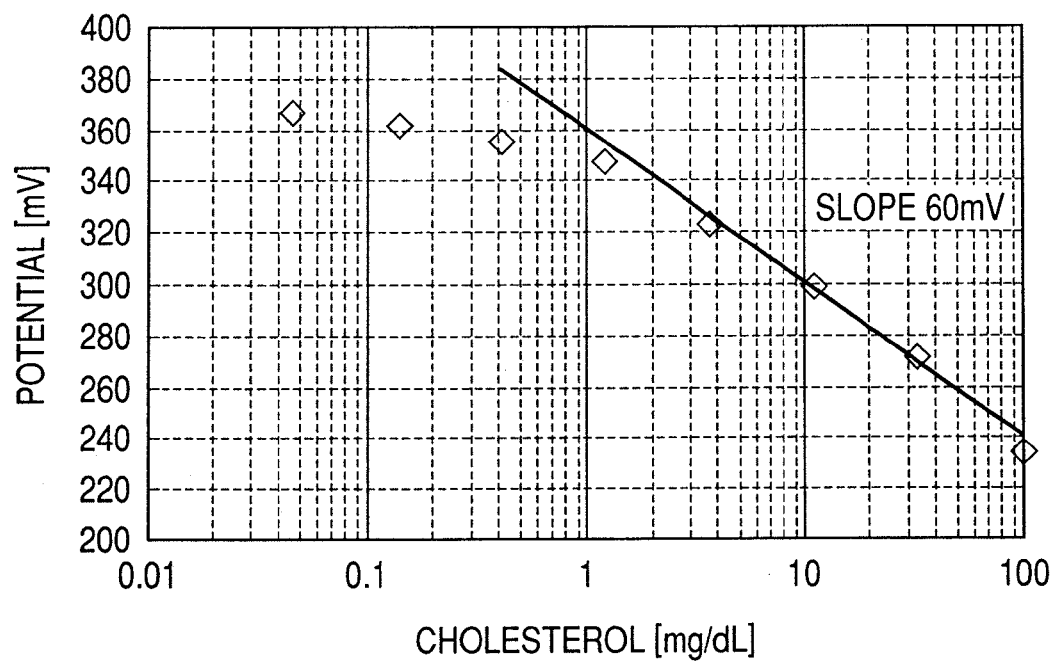
FIG. 14 is a graph showing the result of measuring cholesterol concentration by using a potentiometric enzyme sensor according to the invention.

FIG. 14 shows a result of measuring cholesterol by using the potentiometric enzyme sensor according to the invention. In this embodiment, measurement was conducted by the constitution of apparatus shown in FIG. 1. 11-FUT was used for the redox compound immobilized through the insulative molecules. A silver chloride electrode using saturated potassium chloride as the internal solution was used for the reference electrode. As the measuring solution, a mixed solution which contains 20 µl of 0.046 to 100 mg/dl cholesterol solution (dissolved in 2% aqueous solution of Triton X-100), 10 µl of 3 mg/ml NAD solution (dissolved in 0.3 M aqueous solution of Tris-HCl (pH 8.5)), 3 µl of 100 mM aqueous solution of potassium ferricyanide, and 1 µl of 100 U/ml aqueous solution of diaphorase was used. 1 µl of 10 mg/ml cholesterol dehydrogenase was injected by using the sample solution injector, and the potential difference between the reference electrode and the gold electrode 600 sec after the injection was plotted in FIG. 14. A slope sensitivity of 60 my was obtained to the cholesterol concentration (abscissa), and it can be seen that a potential in accordance with the cholesterol concentration is generated in a range from 1 to 100 mg/dl. In this measurement, as a result of the occurrence for the reaction: cholesterol+NAD→cholestenone+NADH catalyzed by the cholesterol dehydrogenase, the reaction: NADH+ferricyan→NAD+ferrocyan catalyzed by diaphorase, and the reaction: ferrocyan+ferrocene (oxidation form)→ferricyan+ferrocene (reduced form) on the surface of the gold electrode, the surface potential of the gold electrode was changed in accordance with the cholesterol concentration. By using this principle, the cholesterol concentration can be measured as the potential change.

Figure 15:
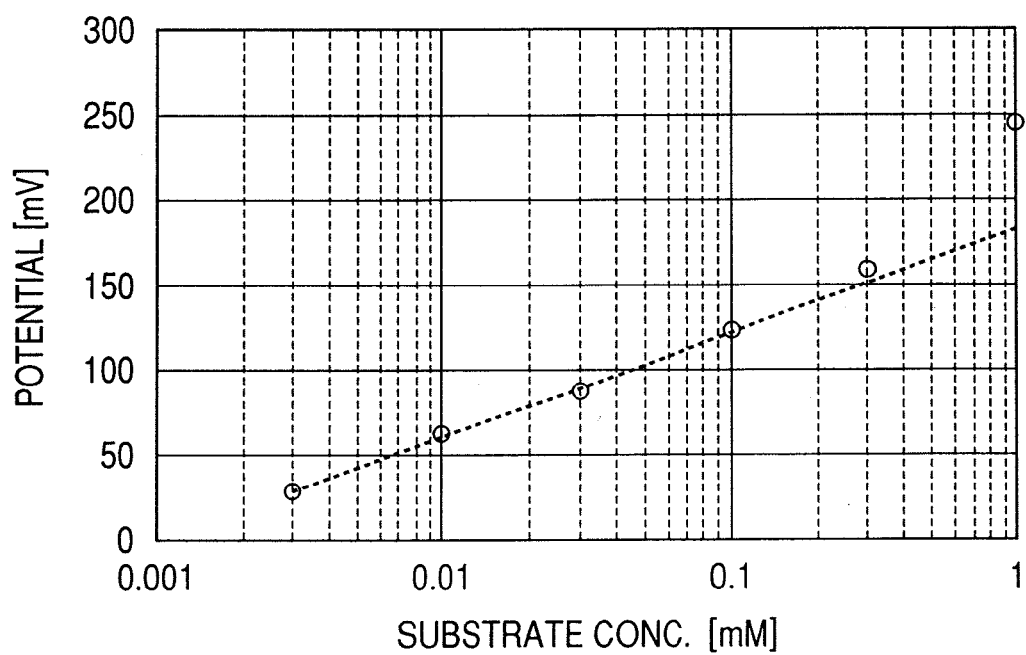
FIG. 15 is a graph showing the result of measuring Fru-Val-His substrate by using a potentiometric enzyme sensor according to the invention.

FIG. 15 shows the result of measuring Fru-Val-His peptide obtained by treating hemoglobin $A_{1c}$ with a protease enzyme by using the potentiometric enzyme sensor according to the invention. In this embodiment, measurement was conducted by the constitution of apparatus shown in FIG. 2. 11-FUT was used for the redox compound immobilized through the insulative molecules, a PBS solution was used for the measuring solution, Fluctosyl-peptide Oxidase (FPDX) was used as the enzyme, 1 mM potassium ferrocyanide was used for the water soluble redox compound, and a silver chloride electrode using saturated potassium chloride as the internal solution was used for the reference electrode. An aqueous solution of Fru-Val-His peptide substrate was used for the sample solution. The abscissa shows the final concentration of the substrate and the ordinate shows the potential difference before injection of the measured substance and 600 sec after injection. This result shows that a potential in accordance with the concentration of the substrate is generated. The slope sensitivity in this case was about 60 mV and it can be seen that the potential is generated in accordance with Nernst's equation.

Figure 16:
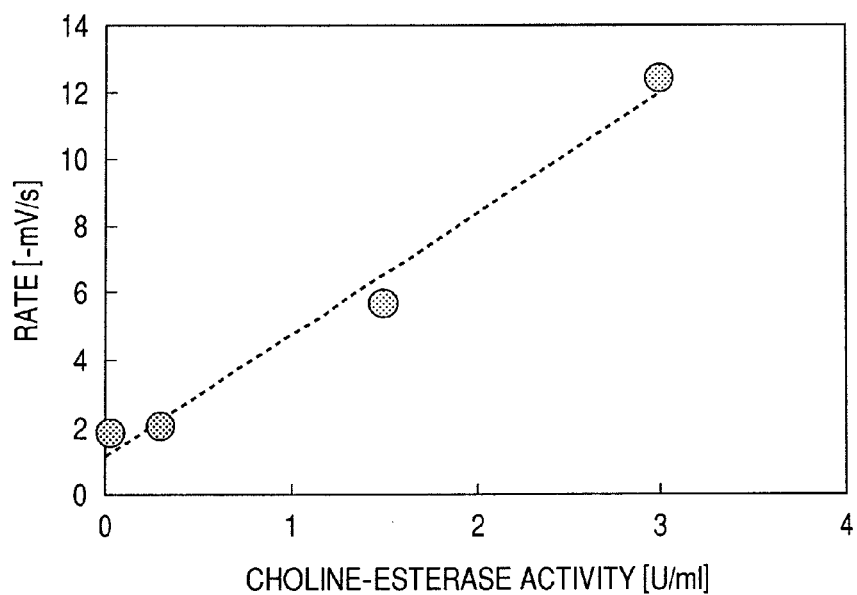
FIG. 16 is a graph showing the result of measuring cholinesterase activity by using a potentiometric enzyme sensor according to the invention.

FIG. 16 shows the result of measuring the cholinesterase activity by using the potentiometric sensor in which the redox compound was immobilized through the insulative molecules on the working electrode according to the invention. In this example, measurement was conducted with the constitution of apparatus shown in FIG. 7B. 11-FUT was used for the redox compound immobilized through the insulative molecules on the gold electrode, PBS (phosphate buffered saline) containing acetyl thiocholine at a concentration of 1 mg/ml (5.06 mM) was used for the measuring solution, and a silver chloride electrode using saturated potassium chloride as the internal solution was used for the reference electrode. An acetylcholinesterase solution was used for the sample solution. When the sample solution is injected into the measuring solution, acetylthiocholine is decomposed into thiocholine and acetic acid by acetylcholinesterase in the sample solution. When thiocholine is produced, since thiocholine acts as a reducing agent to ferrocene immobilized on the working electrode, the surface potential of the working electrode is lowered. On the other hand, since acetylthiocholine has no thiol groups at the terminal, it does not act as the reducing agent and gives no effect on the surface potential of the working electrode. Accordingly, the potential was lowered in accordance with the activity of acetylcholinesterase in the sample solution. FIG. 16 shows the activity of acetylcholinesterase in the sample solution on the abscissa and the rate of potential change just after the injection of the sample solution on the ordinate. The rate of potential change in proportion with the activity of acetylcholinesterase was observed. From the result, the concentration of acetylcholinesterase can be determined based on the rate of potential change. In addition to the rate of potential change, the quantity of change of the potential difference can also be used and since the quantity of change of the potential difference in proportion to the logarithm of the cholinesterase activity is obtained in this case, a wider dynamic range can be obtained.

As other application example, organophosphate pesticides that inhibit the acetylcholinesterase activity can be measured. A solution containing a sufficient amount of acetylcholine was used for the measuring solution and a solution containing a predetermined amount of acetylcholinesterase and a measured substance is used for the sample solution. In a case where a pesticides that inhibits acetylcholinesterase activity contained in the sample solution, the decomposing rate of acetylthiocholine by acetylcholinesterase is lowered. Accordingly, the concentration of the organophosphate pesticides as the acetylcholinesterase inhibitor contained in the sample solution can be measured based on the decomposing rate of acetylcholine, that is, the rate of the potential change.

Also in a case of using an unmodified gold electrode instead of the gold electrode on which the redox compound is immobilized through the insulative molecules, the potential change due to the bonding of thiocholine to the surface of the gold electrode can be measured. However, the gold electrode is disposed after use in this case. On the other hand, in a case of using the gold electrode on which the redox compound is immobilized through the insulative molecules according to the invention, since thiocholine is not bonded to the surface of the gold electrode, the gold electrode can be used for several times by washing to regenere. For regeneration, potassium ferricyanide or hydrogen peroxide as an oxidizing substance is used preferably.

Figure 17A:
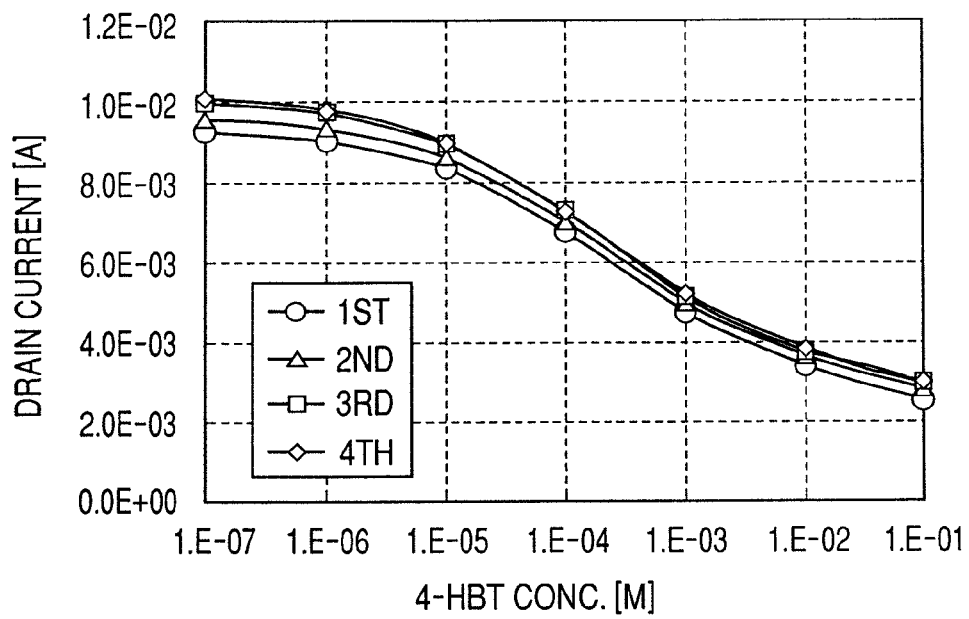
FIG. 17 is a graph showing the result of repetitively measuring a thiol compound by using an FET sensor according to the invention.
Figure 17B:
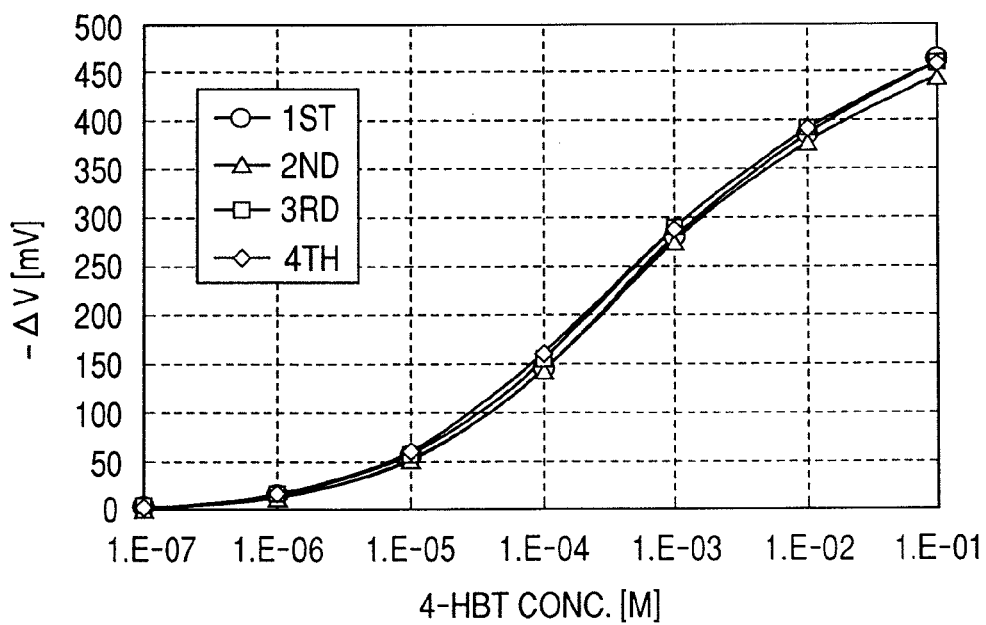

FIG. 17 shows the result of repetitively measuring the concentration of 4-hydroxy-1-butanthiol (4-HBT) as a thiol compound by using an FET sensor in which the redox compound is immobilized through the insulative molecules to the working electrode according to the invention. 11-FUT was used for the redox compound immobilized through the insulative molecules on the gold electrode, a 4-HBT solution (dissolved in PBS) was used for the measuring solution, and a silver chloride electrode using saturated potassium chloride as the internal solution was used for the reference electrode. After washing with 5% aqueous hydrogen peroxide for three times before measurement, measurement was conducted in the order of 4-HBT concentration at $10^{-7}$M, $10^{-6}$M, $10^{-5}$M, $10^{-4}$M, $10^{-3}$M, $10^{-2}$M, and $10^{-1}$M. The result is shown in FIG. 17A (1st time). As the 4-HBT concentration increased, a drain current value was decreased. This is because ferrocene immobilized on the surface of the gold electrode is reduced by 4-HBT and the potential on the surface of the gold electrode was lowered. Again, after washing with 5% aqueous hydrogen peroxide for three times, the concentration of 4-HBT was changed and measured in the same manner. The result is shown in FIG. 17A (2nd time). Like (1st time), a drain current value in accordance with the 4-HBT concentration was observed. In the same manner, when (3rd) and (4th) were measured, same results were also obtained. The drain current values were converted into the surface potential of the gold electrode based on the gate voltage (VG)-drain current (ID) characteristic of the FET measured separately, and the decrement of the voltage ($-\Delta V$) was plotted with $10^{-7}$M as the reference (FIG. 17B). In any measurement, a potential change depending on the 4-HBT concentration was observed, the immobilized redox compound was in an oxidized state by washing with an oxidizing agent such as hydrogen peroxide and it was confirmed that the thiol compound can be measured repetitively. Also in a case of using the unmodified gold electrode instead of the gold electrode on which the redox compound was immobilized through the insulative molecules, the concentration of the thiol compound can be measured due to the potential change by the bonding of the thiol compound to the surface of the gold electrode. However, in this case, the gold electrode is disposed after use. On the other hand, by the use of the gold electrode on which the redox compound was immobilized through the insulative molecules of the invention, since the thiol compound is not bonded to the surface of the gold electrode, the gold electrode can be used for several times by washing and regeneration.

Figure 18:
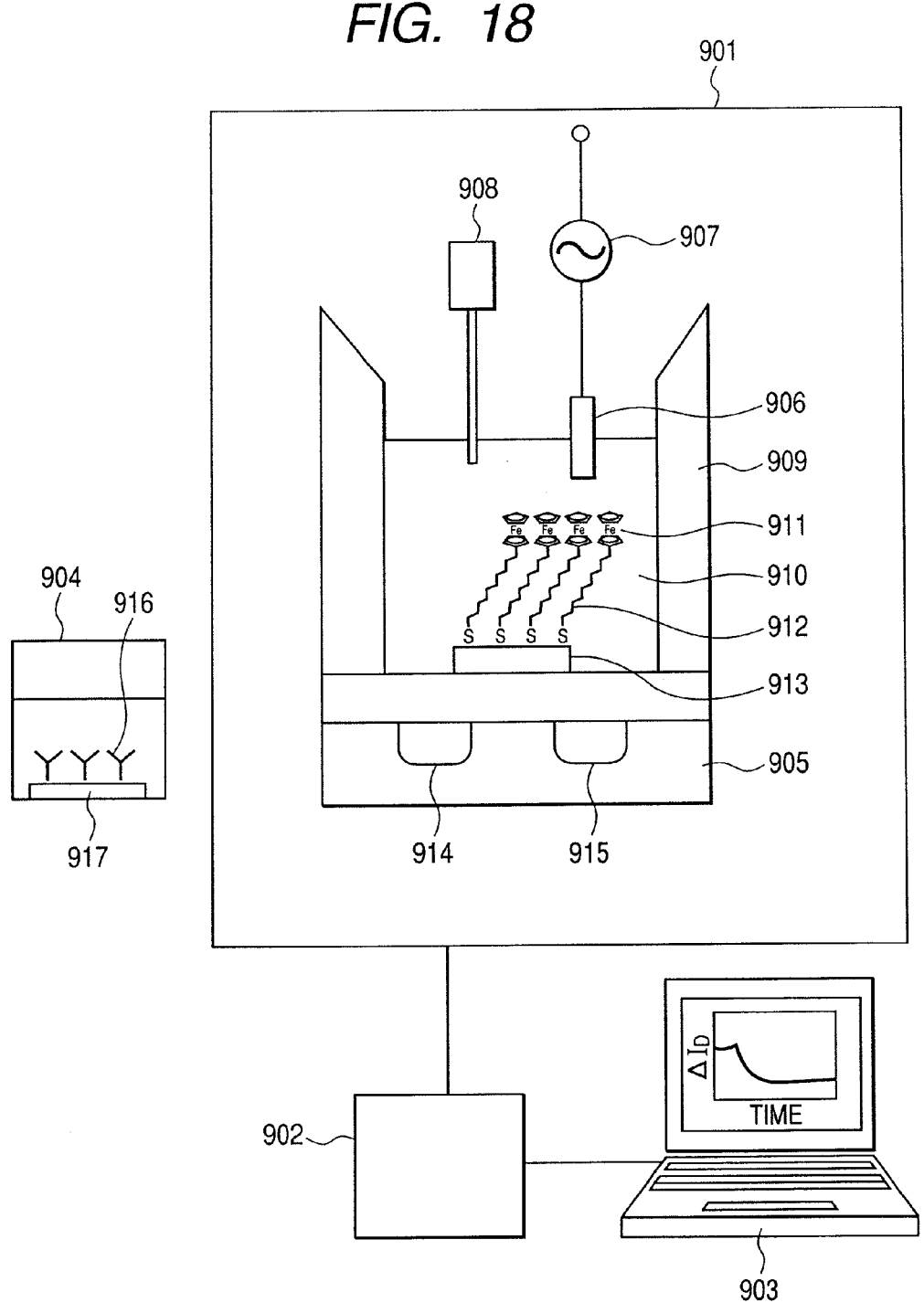
FIG. 18 is a block diagram showing an example of an enzyme immunoassay system by using an FET sensor according to the invention.

FIG. 18 is a block diagram showing an example of an immunoassay system using an FET sensor according to the invention. The analytic system includes a measuring station 901, a signal processing circuit 902, a data processing apparatus 903, and a reactor 904 for a thiol compound producing reaction. In the measuring station 901, there are placed an insulated gate field-effect transistor 905, a reference electrode 906, a power source 907 for applying a high frequency voltage to the reference electrode 906, and a thiol compound solution injector 908 for supplying the solution in the reactor 904. A gold electrode 913 formed on the insulated gate field-effect transistor 905 and a reference electrode 906 are provided in a reaction solution 910 in a measuring cell 909. A redox compound 911 is immobilized through an insulative molecules 912 on the gold electrode. In the reactor 904 for the thiol compound producing reaction, an antibody 916 is immobilized on an antibody immobilizing plate 917. The antibody 916 may be directly immobilized on the inside of the reactor 904.

The measuring procedures are as described below. A sample solution was injected to the reactor 904 for the thiol compound producing reaction, to bind an antigen and the antibody 916 in the sample solution. After a predetermined time, an enzyme labeled antibody solution is injected into the reactor 904 to cause antigen-antibody reaction and form an antibody-antigen-enzyme labeled antibody. Then, the bound enzyme labeled antibody and the free enzyme labeled antibody are separated by exchange of the solution in the reactor 904 and washing of the reactor 904. After exchange of solution and washing in the reactor 904, when the substrate for the labeling enzyme is injected, the substrate is decomposed by the enzyme to produce a thiol compound. After reaction for a predetermined time, the produced thiol compound is introduced by using a thiol compound solution injector 908 to the reaction solution 910 in the measuring cell 909. The thiol compound introduced to the reaction solution 910 in the measuring cell 909 reduces the redox compound 911 immobilized on the gold electrode 913 formed on the insulated gate field-effect transistor 905. As a result, the potential on the gold electrode 913 changes. The current between a source 914 and a drain 915 in the insulated gate field-effect transistor 905 that changes before and after the injection of the produced thiol compound is measured on real time and recorded by the signal processing circuit 902 and the data processing apparatus 903. Since the potential on the gold electrode 913 is determined by the ratio of the oxidized state and the reduced state of the redox compound 911, a potential depending on the concentration of the thiol compound is generated to the gold electrode 913. Accordingly, the amount of the bound labeling enzyme, that is, the amount of the antigen in the sample solution can be obtained by measuring the value of the current between the source 914 and the drain 915 that changes with the potential of the gold electrode 913.

The enzyme immunoassay using the apparatus of the invention is to be described below. In this embodiment, the amount of the antigen was measured indirectly through an enzyme labeled to the antibody by using a sandwich method generally used in immunoassay. After reaction between the antibody immobilized previously on the plate and the antigen in the sample, an enzyme labeled antibody was added to form an antibody-antigen-enzyme labeled antibody. Then, the bound enzyme labeled antibody, and the free enzyme labeled antibody and the free antigen were separated, and the thiol compound as a product of a cyclic reaction between enzyme of the bound enzyme labeled antibody and the substrate was measured by the FET sensor. The samples and the reagents used in this embodiment are shown below. Immobilized antibody: Interleukin 1a (IL-1β) antibody
Sample: Human plasma
Measured substance: IL-1β
Enzyme labeled antibody: Acetylcholinesterase (AchE): IL-1β Fab' Conjugate
Substrate: 2.5 mM Acetylthiocholine
Reaction solution: PBS The reaction conditions and reagent concentrations used herein are mere examples and can be changed properly depending on the constitution of apparatus and the measured substance.

The measuring procedures are as described below. At first, 100 μL of a sample solution (Human plasma) and 100 μL of an enzyme labeled antibody (AchE: IL-1β Fab' Conjugate) were added to a well of a plate on which the IL-1β antibody was immobilized, the plate was covered with a plastic film and they were reacted at 4° C. for overnight. Then, the solution in the well of the plate was discarded and the plate was washed with a washing buffer for 5 to 6 times. An acetylthiocholine solution as a substrate solution for acetylcholine esterase was added to each of the wells and reacted for about 20 min. The reaction solution containing the thiol compound produced by the reaction was introduced into a reaction cell in which the FET sensor was dipped, and the potential change on the gold electrode due to the redox reaction between the thiol compound and the redox compound immobilized on the gold electrode was measured thereby obtaining a concentration of the produced thiol compound. Since the concentration of the produced thiol compound is in proportion with the enzyme concentration of the antibody-antigen-enzyme labeled antibody, the amount of antigen can be determined quantitatively.

Figure 19A:
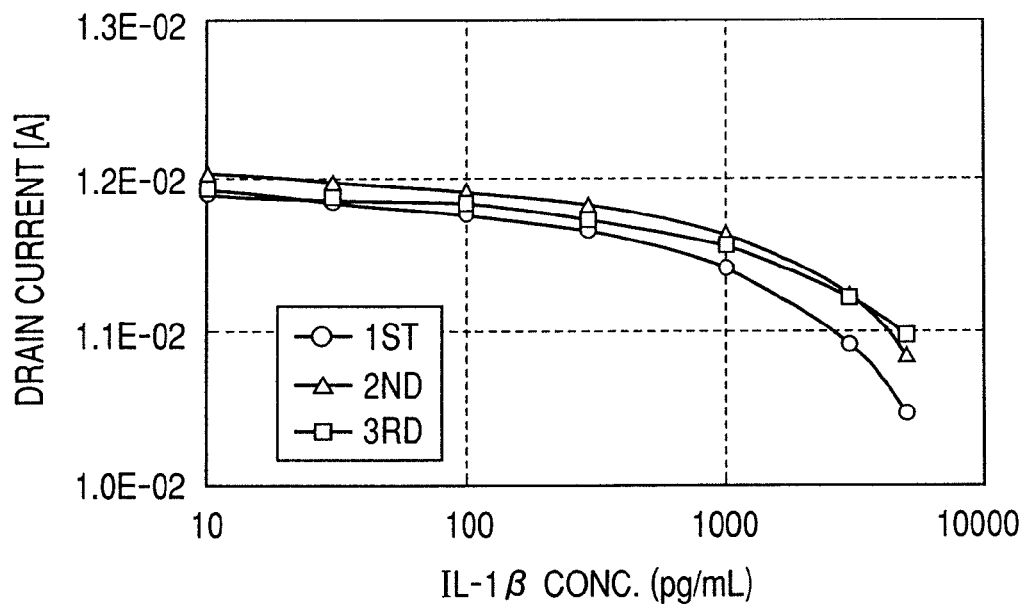
FIG. 19 is a graph showing the result of repetitively measuring IL-1β by using an FET sensor according to the invention.
Figure 19B:
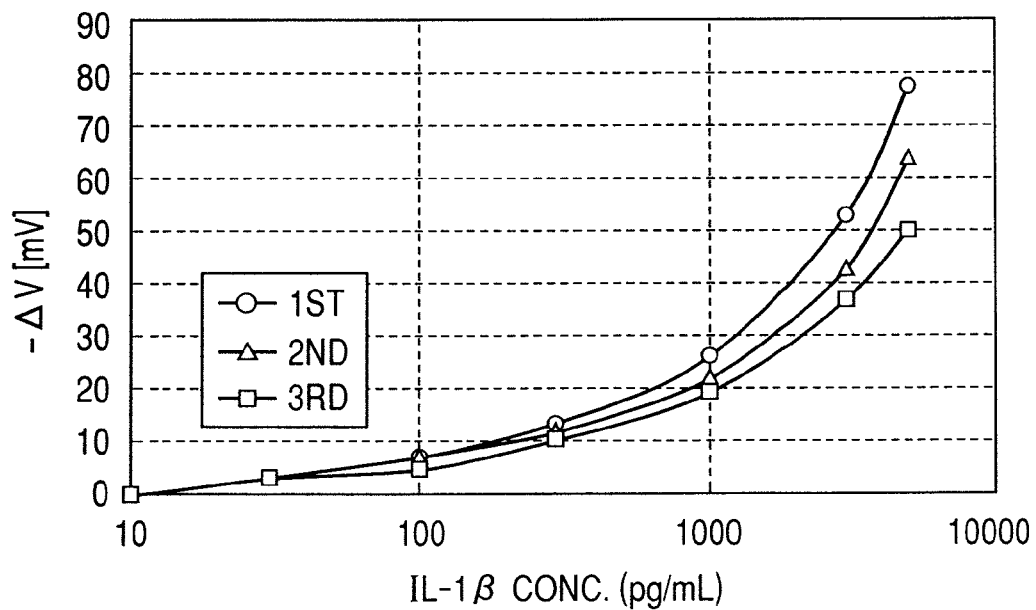

Upon measurement by the FET sensor, 11-FUT was used for the redox compound immobilized through the insulative molecules, and an Ag/AgCl reference electrode was used as the reference electrode. An AC voltage with a center voltage of 100 mV and an amplitude voltage of 100 mV, and at a frequency of 1 MHz was applied to the reference electrode. 1.0V was applied between the source and the drain, and the drain current value 1 min after the start of the measurement was recorded. The procedures were conducted for IL-1β as the antigen at concentrations of 10, 30, 100, 300, 1,000, 3,000, and 5,000 pg/ml orderly. Then, the FET sensor was washed with 5% aqueous hydrogen peroxide, and the concentration of IL-1β was measured again. FIG. 19A shows the result of the measurement conducted for three times. In each of measurements, a correlation that the drain current value decreases as the IL-1β concentration increases was obtained and a similar result was obtained in any measurement. The result was converted to the surface potential of the gold electrode by using the FET gate voltage (VG)-drain current (ID) characteristics measured separately, and the decrement of the potential ($-\Delta V$) was plotted with 10 pg/ml for the IL-1β concentration as the standard (FIG. 19B). In any measurement, the potential change depending on IL-1β concentration was observed, and it was confirmed that the immobilized redox compound was in the oxidized state by washing with the oxidizing agent such as hydrogen peroxide and the concentration of the thiol compound, that is, the antigen could be measured repetitively.

What is claimed is:

1. A potentiometric sensor comprising:
    a vessel to which a measuring solution containing an object for measurement is introduced,
    a working electrode in contact with the measuring solution in the vessel,
    a reference electrode in contact with the measuring solution in the vessel, and
    a potentiometer connected to the working electrode and the reference electrode for measuring a potential difference between the working electrode and the reference electrode,
    an enzyme in the measuring solution, wherein the enzyme is not immobilized on the working electrode or the reference electrode, and the enzyme is configured to produce an oxidized substance or a reduced substance for measurement,
    wherein a redox compound is immobilized through insulative molecules on the working electrode.

2. A potentiometric sensor comprising:
    a vessel to which a measuring solution containing an object for measurement is introduced,
    a working electrode in contact with the measuring solution in the vessel,
    a reference electrode in contact with the measuring solution in the vessel, and
    a potentiometer connected to the working electrode and the reference electrode for measuring a potential difference between the working electrode and the reference electrode,
    wherein a redox compound is immobilized through insulative molecules on the working electrode, and
    wherein an enzyme configured to produce an oxidized substance or a reduced substance for measurement is contained in the vessel.

3. The potentiometric sensor according to claim 2, wherein the redox compound is a ferrocene derivative.

4. The potentiometric sensor according to claim 2, wherein the insulative molecules comprise a carbon chain.

5. The potentiometric sensor according to claim 2, wherein the working electrode is formed of carbon or a noble metal.

6. The potentiometric sensor according to claim 2, wherein the object for measurement is an ingredient contained in a biological sample.

7. The potentiometric sensor according to claim 6, wherein the biological sample is blood or urine.

* * * * *